US006927247B2

(12) United States Patent
Starnes, Jr. et al.

(10) Patent No.: US 6,927,247 B2
(45) Date of Patent: Aug. 9, 2005

(54) ORGANIC THIOL METAL-FREE STABILIZERS AND PLASTICIZERS FOR HALOGEN-CONTAINING POLYMERS

(75) Inventors: William Herbert Starnes, Jr., Williamsburg, VA (US); Soungkyoo Kim, Haverford, PA (US)

(73) Assignee: The College of William and Mary, Williamsburg, VA (US)

( * ) Notice: Subject to any disclaimer, the term of this patent is extended or adjusted under 35 U.S.C. 154(b) by 168 days.

(21) Appl. No.: 10/460,731

(22) Filed: Jun. 12, 2003

(65) Prior Publication Data

US 2003/0220429 A1 Nov. 27, 2003

Related U.S. Application Data

(63) Continuation-in-part of application No. 10/171,744, filed on Jun. 14, 2002, now Pat. No. 6,747,081, which is a continuation-in-part of application No. 09/884,306, filed on Jun. 19, 2001, now Pat. No. 6,762,231, which is a continuation-in-part of application No. 09/737,973, filed on Dec. 15, 2000, now Pat. No. 6,667,357.

(51) Int. Cl.$^7$ .......................... C08K 5/37; C07C 321/06
(52) U.S. Cl. ....................... 524/289; 524/302; 524/303; 524/304; 524/305; 524/368; 524/392; 560/9; 568/63; 568/67
(58) Field of Search .................. 524/289, 302–305, 524/368, 392; 560/9; 568/63, 67

(56) References Cited

U.S. PATENT DOCUMENTS

| | | | |
|---|---|---|---|
| 2,483,984 A | 10/1949 | Searles, Jr. | |
| 3,136,740 A | 6/1964 | Klemchuk et al. | |
| 3,167,527 A | 1/1965 | Hechenbleikner | |
| 3,242,133 A | 3/1966 | Lindsey | |
| 3,445,419 A | 5/1969 | Vanderlinde | |
| 3,503,924 A | 3/1970 | Pollock et al. | |
| 3,507,827 A | 4/1970 | Pollock et al. | |
| 3,585,038 A | 6/1971 | Cescon et al. | |
| 3,652,733 A | 3/1972 | Davenport | |
| 3,734,753 A | 5/1973 | Greco et al. | |
| 3,875,109 A | 4/1975 | Bridgland et al. | |
| 3,917,553 A | 11/1975 | Thompson | |
| 3,928,285 A | 12/1975 | Gough et al. | |
| 3,966,794 A | 6/1976 | Larsen | |
| 3,979,359 A | 9/1976 | Kugele et al. | |
| 4,098,763 A | 7/1978 | Starnes, Jr. | |
| 4,132,812 A | 1/1979 | Mathias | |
| 4,198,305 A | 4/1980 | Okorodudu | |
| 4,202,806 A | 5/1980 | Yoshida et al. | |
| 4,264,482 A | 4/1981 | Homan | |
| 4,333,987 A | 6/1982 | Kwart et al. | |
| 4,338,226 A | 7/1982 | Worschech et al. | |
| 4,412,897 A | 11/1983 | Kornbaum et al. | |
| 4,576,984 A | 3/1986 | Bresser et al. | |
| 4,616,046 A | 10/1986 | Kornbaum et al. | |
| 4,625,059 A | 11/1986 | Shibano et al. | |
| 4,711,920 A | 12/1987 | Kugele et al. | |
| 4,849,463 A | 7/1989 | Kemper | |
| 4,873,005 A | 10/1989 | Hyde | |
| 4,948,827 A | 8/1990 | Christidis | |
| 4,963,594 A | 10/1990 | Gay | |
| 4,973,619 A | 11/1990 | Kemper | |
| 5,006,436 A | 4/1991 | Hung et al. | |
| 5,030,671 A | 7/1991 | Wehner et al. | |
| 5,057,567 A | 10/1991 | Fisch et al. | |
| 5,057,622 A | 10/1991 | Chisholm et al. | |
| 5,198,486 A | 3/1993 | Chisholm et al. | |
| 5,216,058 A | 6/1993 | Visneski | |
| 5,294,666 A | 3/1994 | Okada et al. | |
| 5,414,030 A | 5/1995 | Kotani et al. | |
| 5,536,767 A | 7/1996 | Beckman et al. | |
| 5,594,088 A | 1/1997 | Nagata et al. | |
| 6,232,380 B1 | 5/2001 | Conroy et al. | |
| 6,326,518 B1 | 12/2001 | Duvall et al. | |
| 6,476,183 B2 | 11/2002 | Bakkeren et al. | |

FOREIGN PATENT DOCUMENTS

| | | |
|---|---|---|
| DE | 32 47 736 | 7/1984 |
| EP | 0 133 130 | 2/1985 |
| EP | 0 205 261 | 12/1996 |
| EP | 0 890 608 A2 | 1/1999 |
| EP | 0 945 484 A1 | 9/1999 |
| GB | 1024270 | 1/1965 |
| JP | 64-63002 | 4/1979 |
| JP | 63-128002 | 5/1988 |
| JP | 63-241055 | 6/1988 |
| JP | 01090167 A | 4/1989 |
| WO | WO 99/09094 | 2/1999 |

OTHER PUBLICATIONS

The conductive sulfur/carbon mixture cathode. An efficient synthesis of thiophenes and related compounds from acetylenes. La Guilanton et al. Lab. Electrochim. Org., Univ. Cathol. Quest, Angars 49005, Fr. Tetrahedron Letters (1986) 27 (20) 2261–2.

Abstract from 36 Plastics Manufacturer, vol. 86, 1977 pp. 44–45 entitled "Stabilizers for Chlorine–Containing Resins."

Stabilization of Poly(vinyl chloride) by Thiols. A Mechanistic Study, vol. 11, No. 2. W. H. Starnes, Jr., I. M. Plitz, D. C. Hische, D. J. Freed, F. C. Schilling, and M. L. Schilling, Bell Laboratories, Murray Hill, New Jersey, pp. 373–382, Mar.–Apr. 1978.

A Novel Initiation Process for the Nonoxidative Thermal Dehydrochlorination of Poly(vinyl chloride): Apparent Intermediacy of a Cyclic Chloronium Ion by Starnes et al., Polymer Preprints (American Chemical Society, Division of Polymer Chemistry), 21 (2), pp. 138–139, 1980.

(Continued)

*Primary Examiner*—Peter Szekely
(74) *Attorney, Agent, or Firm*—Hudak, Shunk & Farine Co.

(57) ABSTRACT

Organic thiol compounds including mercaptophenylcarboxylates are disclosed which can be utilized to plasticize and/or stabilize halogen-containing polymer compositions, especially poly(vinyl chloride) compositions. Compounds of the present invention are utilized in polymers normally susceptible to deterioration and color change, which typically occurs during processing of the polymer or exposure to certain environments.

20 Claims, No Drawings

OTHER PUBLICATIONS

Mechanistic Aspects of the Degradation and Stabilisation of Poly(vinyl chloride) by W. H. Starnes, Jr., Developments in Polymer Degradation—3; N. Grassie, Ed.; Applied Science: London, U.K., Chapter 5, pp. 135–171, 1981.

Primary Event in the Thermal Dehydrochlorination of Pristine Poly(vinyl chloride): Intermediacy of a Cyclic Chloronium Ion by Raghavachari, et al., Journal American Chemical Society, vol. 104, pp. 5054–5056, 1982.

An Alternative Synthesis of Tiopinac, T. Craig Thurber et al., Contribution No. 587, Development Research Laboratory, Institute of Organic Chemistry, Jul.–Aug. 1982, pp. 961–965.

Thermal Stabilization of PVC by "Plasticizer Thiols", W. H. Starnes, Jr. et al., Departments of Chemistry and Applied Science, Journal of Vinyl & Additive Technology, Dec. 2001, vol. 7, No. 4, pp. 250–253.

Heat Stabilization and Plasticization by "Plasticizer Thiols," A Remarkable New Class of Nonmetallic Additives for PVC, W. H. Starnes et al., Departments of Chemistry and Applied Science, Polymer Preprints 2001.

Nonmetallic Primary Heat Stabilizers for Poly(vinyl chloride), W. H. Starnes, Jr. et al., Department of Chemistry and Department of Applied Scicne, Mar. 24–27, 2002, Additives 2002 Conference, pp. 1–7.

ORGANIC THIOL METAL-FREE STABILIZERS AND PLASTICIZERS FOR HALOGEN-CONTAINING POLYMERS

CROSS REFERENCE

This application is a continuation-in-part of prior application Ser. No. 10/171,744 filed Jun. 14, 2002, now U.S. Pat. No. 6,747,081, which is a continuation-in-part of prior application Ser. No. 09/884,306, filed Jun. 19, 2001, now U.S. Pat. No. 6,762,231, which is a continuation-in-part of prior application Ser. No. 09/737,973, filed Dec. 15, 2000, now U.S. Pat. No. 6,667,357, and all entitled "Organic Thiol Metal-Free Stabilizers and Plasticizers for Halogen-Containing Polymers."

FIELD OF THE INVENTION

The present invention relates to mercaptophenylcarboxylates and other organic thiol compounds and the preparation thereof. The organic thiol compounds are utilized to plasticize and/or heat stabilize halogen-containing polymer compositions especially poly(vinyl chloride) compositions. The compositions are substantially free or free of metal-based stabilizers, Lewis acids and terpenes. The compounds of the present invention are ideally utilized in polymers normally susceptible to deterioration and color change which can occur during processing of the polymer or exposure of the polymer to certain environments and surprisingly also serve as excellent plasticizers.

BACKGROUND OF THE INVENTION

It is well known that chlorine-containing resins, particularly poly(vinyl chloride) polymers and copolymers, are unstable to heat and light and that the physical properties thereof are degraded upon exposure thereto. This degradation is typically manifested by development of or change in color. It is particularly noticeable in unstabilized polymers, i.e., polymers which do not contain stabilizers. Degradation or discoloration during processing is particularly undesirable in clear or lightly colored plastics. Therefore, it is desirable to prevent or inhibit the discoloration of plastics during processing so as to achieve useful products free of discoloration.

In order to minimize the discoloration and deterioration of various halogen-containing polymers such as vinyl chloride polymers and copolymers, various stabilizers such as lead-, cadmium-, and tin-based stabilizers have been developed and utilized. However, in recent years environmental pollution caused by the toxicity of the heavy metal residues and ecological considerations have stimulated further evaluation of such compounds and generated a search for alternative approaches.

Various compounds have been proposed for use in stabilizing halogen-containing polymers:

U.S. Pat. No. 3,928,285 to Gough et al. relates to a synergistic stabilizer composition comprising an organotin borate and an organic thiol.

U.S. Pat. No. 4,948,827 to Christidis relates to a thiophenol, prepared by reduction of tertiary butyl-4-toluenesulfonyl-2-chloride with the zinc-sulfuric acid couple, which reportedly can be used as a stabilizer for vinyl chloride polymers, as a chain-transfer agent, and as a peptizer.

European Patent Application No. EP 0 890 608 A2 relates to both flexible and rigid vinyl chloride polymer compositions incorporating a latent mercaptan-containing heat stabilizer which are reportedly substantially free from the offensive odor typically associated with mercaptans and are protected during processing by the degradation products of the latent (i.e., blocked) mercaptan, which include a free mercaptan.

European Patent Application No. EP 0 945 484 A1 relates to compositions comprising halogen-containing polymers such as PVC resins which are reportedly stabilized against heat by a synergistic combination of a free mercaptan and a metal-based stabilizer and/or a Lewis acid such as zinc chloride.

SUMMARY OF THE INVENTION

Organic thiol compounds and routes for their preparation are disclosed herein. The organic thiol compounds of the present invention, when blended with a halogen-containing polymer such as poly(vinyl chloride) or derivatives thereof, provide numerous advantages which include serving as plasticizers, heat stabilizers, and dehydrochlorination retarders. The organic thiol compounds of the present invention have a substantially reduced or even lack a characteristic odor typically associated with thiol compounds. In a preferred embodiment, the organic thiols are mercaptophenylcarboxylates.

DESCRIPTION OF THE PREFERRED EMBODIMENTS

Aromatic

The organic thiols of the present invention are aromatic compounds having at least one sulfhydryl group attached either directly or indirectly to an aromatic ring. The aromatic compound may contain one or more aromatic rings and at least one sulfhydryl substituent, as well as other groups such as an ester group, and the like. The organic thiols can generally be described by the formula:

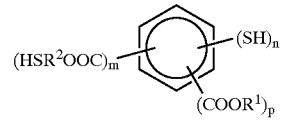

Formula I wherein $R^1$ and $R^2$, independently, comprise straight chain or branched alkyls having from 1 or 2 to about 15 carbon atoms, and preferably from about 4 to about 15 carbon atoms, or an aromatic or a substituted aromatic having from about 6 to about 15 carbon atoms and wherein, independently, n is either 0, 1, 2, or 3, m is either 0, 1, 2, or 3, and p is either 0, 1, 2, or 3, with the proviso that m+n+p=6 or less. It is to be understood that when, independently, m, n, and/or p are greater than 1, the individual repeat groups are each attached to a different carbon atom on the benzene ring.

Independent exemplifications of $R^1$ and $R^2$ are 2-ethylhexyl, isooctyl, isodecyl, benzyl and butyl.

Examples of compounds which can be formed from the above formula include:

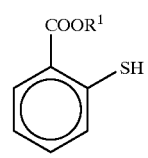

1

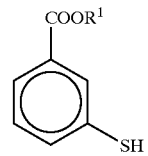

2

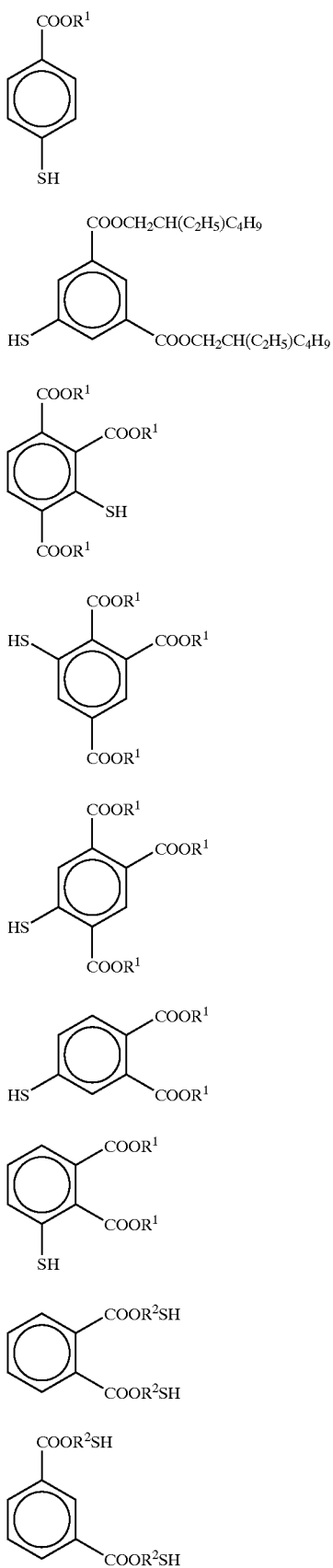

The various compounds of the above-disclosed general formula wherein m=0 can be synthesized substantially as follows. In a first step, a desired amount of an hydroxy aromatic acid is placed in a reaction vessel together with a large molar excess of an alcohol having from 1 to about 3 carbon atoms, preferably methanol or ethanol. From about 0.05 to about 0.5 mole, per mole of the starting acid, of a very strong acid, i.e., one having a concentrated pH of at least 1 to about 3, such as $H_2SO_4$, para-toluenesulfonic acid, or hydrochloric acid, is added to the mixture, and the mixture is then heated either under air or preferably under inert conditions, such as under nitrogen, generally to the reflux temperature of the alcohol, for a sufficient length of time until the reaction is complete, a condition which can be established through periodic analysis.

The hot solution is then poured into a quantity of ice water. Then, the precipitate is filtered off and washed on the filter until the pH of the wash liquid is neutral. The filtered product is then dried to give an hydroxy aromatic ester, which can be purified further by conventional methods, if desired.

A desired amount of the above-noted ester is added to a reaction vessel along with an N,N-dialkylthiocarbamoyl halide such as N,N-dimethylthiocarbamoyl chloride (about 1–3 moles per mole of ester), a base such as DABCO (about 1–3 moles per mole of ester), and N,N-dimethylformamide (about 1–3 liters per mole of ester). The mixture is stirred at room temperature (e.g., 15° C. to about 30° C.) for a suitable reaction time, and a suitable quantity of water is then added to induce precipitation of a solid which is filtered off and washed on the filter until the pH of the wash liquid is neutral. The resulting second step intermediate product (the corresponding O-substituted N,N-dimethylthiocarbamate) is subsequently dried.

The second step intermediate product is transferred to a suitable reaction vessel and heated preferably in an oil bath or the like to a temperature from about 180° C. to about 250° C. and desirably from about 220° C. to about 235° C. until the reaction is complete, generally in about 20 minutes to about 2 hours. Then, after cooling to about 60° C. to about 90° C., the reaction vessel is purged with nitrogen or other chemically unreactive gas, and an aqueous solution of a base such as NaOH or KOH is subsequently added in an amount that is at least sufficient to cause hydrolysis of the thiocarbamate and ester groups. The mixture is heated under reflux to induce complete reaction and then cooled to room temperature and acidified to a pH generally less than 4 in any manner such as with a 10 percent aqueous solution utilizing an acid as stated above. The recovered mercapto acid product from the third step is washed with suitable quantities of water and dried, preferably under a vacuum.

In the final step of the synthesis, the intermediate product from the third step is added to a reaction vessel equipped with a suitable stirring apparatus, a water separator, and a reflux condenser, along with an alkyl alcohol having from 1 to 15 carbon atoms in an amount from about 1 to about 2 molar equivalents per carboxyl group in the mercapto acid, benzene or other suitable entraining agent for water (about 0.5 to 2 L per mole of mercapto acid), and a strong acid (about 0.1 to 0.3 mole per mole of mercapto acid) as defined above. The mixture is heated to the reflux temperature for a sufficient time to induce extensive reaction, typically approximately three hours, or until all the solid is dissolved. The solution is cooled to room temperature and poured into ice water, and the organic layer is washed in succession with a $NaHCO_3$ or $Na_2CO_3$ solution and water. The organic layer is dried over a drying agent such as anhydrous $MgSO_4$. The dried solution is decolorized with activated carbon, filtered, and distilled to remove the benzene and other volatile impurities. The final product is generally an oil or low melting solid having a structure defined by the general formula of the present invention.

When m in the general formula is unequal to 0, the $HSR^2OOC$ groups of the thiols of this invention can be introduced by the direct esterification of COOH groups with thioalkanols ($HSR^2OH$), using methods that are well-known to those skilled in the art. For example, compound 11 in which $R^2$ is —$(CH_2)_6$— has been prepared by the esterification of isophthalic acid with two molar equivalents of 6-mercapto-1-hexanol in the presence of a catalytic amount of concentrated $H_2SO_4$.

Bis(2-ethylhexyl) 5-mercaptoisophthalate is one such compound which is disclosed by the general formula of the present invention when n is 1, m is 0, p is 2, and $R^1$ is 2-ethylhexyl, and is also shown as specific formula 4. The synthetic route disclosed hereinbelow for preparation of the bis(2-ethylhexyl) 5-mercaptoisophthalate compound is based in part on a Newman-Kwart reaction, as in the general route described above.

Bis(2-ethylhexyl) 5-mercaptoisophthalate can be synthesized as follows:

To a 1-L round-bottom flask equipped with a magnetic stirring bar were added 187.8 g (1 mol) of 5-hydroxyisophthalic acid commercially available from Aldrich (purity approximately 97%) and 500 mL (12.3 mol) of methanol. After the addition of 28 mL of concentrated $H_2SO_4$, the mixture was heated to the reflux temperature and stirred under reflux for 4 hours. The hot solution was poured into 500 mL of ice water. Then, the white solid product was filtered off and washed on the filter with several portions of water until the pH of the wash liquid was neutral. The product was dried under vacuum, preferably at 60° C. overnight, to give 206.8 g of dimethyl 5-hydroxyisophthalate. Testing on the composition revealed the following data: mp 164–166° C.; GC purity >99%; yield 98.2%; $^1$H NMR (in $CDCl_3$+DMSO-$d_6$ w/TMS, ppm): 3.68 (s, 6H, $OCH_3$), 7.45 (s, 2H, CH), 7.89 (s, 1H, CH), 9.35 (broad, 1H, OH); $\{^1H\}^{13}C$ NMR (in $CDCl_3$+DMSO-$d_6$ w/TMS, ppm): 51.92 ($OCH_3$), 120.50 (C4, C6), 121.10 (C2), 131.15 (C1, C3), 157.36 (C5), 165.85 (COOR); $^1$H-$^{13}$C NMR (in $CDCl_3$+DMSO-$d_6$ w/TMS, ppm): 51.92 (quartet, $OCH_3$, $^1J_{CH}$=147 Hz), 120.50 (d, C4, C6, $^1J_{CH}$=164.4 Hz), 121.10 (d, C2, $^1J_{CH}$=168.3 Hz), 131.15 (s, C1, C3), 157.36 (s, C5), 165.85 (s, COOR); GC-MS (in acetone): 210 ($M^+$).

To a 150-mL round-bottom flask equipped with a magnetic stirring bar were added dimethyl 5-hydroxyisophthalate, N,N-dimethylthiocarbamoyl chloride, DABCO (1,4-diazabicyclo[2.2.2]octane), and 50 mL of N,N-dimethylformamide. The mixture was stirred at room temperature for 5 hours, and 100 mL of water then was added slowly. The orange solid gradually disappeared, and the solution became light brown. An additional 100 mL of water was added to induce the precipitation of a white solid, which was filtered off and washed on the filter with portions of water until the pH of the wash liquid was neutral. The product was dried, preferably under vacuum at 60° C. overnight, to give 1-O-3,5-bis(methoxycarbonyl)phenylene N,N-dimethylthiocarbamate as a white powder. Testing of the compound revealed the following: mp 114.5–116.5° C.; $^1$H NMR (in $CDCl_3$w/TMS, ppm): 3.38 (s, 3H, $NCH_3$), 3.46 (s, 3H, $NCH_3$), 3.94 (s, 6H, $OCH_3$), 7.93 (s, 2H, CH), 8.58 (s, 1H, CH); $\{^1H\}^{13}C$ NMR (in $CDCl_3$ w/TMS, ppm): 38.85 ($NCH_3$), 43.39 ($NCH_3$), 52.51 ($OCH_3$), 127.96 (C4), 128.36 (C2, C6), 131.54 (C3, C5), 153.86 (C1), 165.30 (COOR), 186.84 ($OC(S)NR_2$).

As shown by the following table, reaction yield for 1-O-3,5-bis(methoxycarbonyl)phenylene N,N-dimethylthiocarbamate varied as a function of the molar ratio of the reactants.

TABLE 1

Molar Ratio of the Reactants vs. Reaction Yield

| Dimethyl Ester,a g (mmol) | N,N-Dimethyl-thiocarbamoyl Chloride, g (mmol) | DABCO, g (mmol) | Molar Ratio | Yield, g (%) |
|---|---|---|---|---|
| 5.50 (26.2) | 9.60 (77.0) | 8.70 (77.0) | 1/3/3 | 7.60 (97.7) |
| 5.00 (23.8) | 3.30 (26.2) | 8.00 (71.4) | 1/1.1/3 | 6.54 (92.5) |
| 5.00 (23.8) | 3.30 (26.2) | 5.34 (47.6) | 1/1.1/2 | 6.42 (90.7) |
| 5.00 (23.8) | 2.95 (23.8) | 2.95 (26.3) | 1/1/1.1 | 5.13 (72.4) |
| 4.82 (22.9) | 3.12 (25.2) | 3.86 (34.4) | 1/1.1/1.5 | 4.38 (64.0) | a= Dimethyl 5-hydroxyisophthalate.

In a test tube containing a magnetic stirring bar, 0.1 g (0.336 mmol) of 1-O-3,5-bis(methoxycarbonyl)phenylene N,N-dimethylthiocarbamate was heated in an oil bath at a constant temperature, preferably about 230–235° C., for a selected time, preferably least 20 minutes. As can be seen from the following table, reaction yield varied as a function of time and temperature.

TABLE 2

Reaction Yield of 1-S-3,5-bis(methoxycarbonyl)phenylene N,N-dimethylthiocarbamate As a Function of Temperature and Time

| Temperature, ° C. | Time, min | Yield, %a |
|---|---|---|
| 176 | 20 | No reaction |
| 200 | 20 | <5 |
| 208 | 20 | <5 |
| 220 | 20 | 30 |
| 230 | 20 | 55 |
| 240 | 20 | Decomposition |
| 230 | 40 | 75 |
| 230 | 60 | 90 |
| 232 | 60 | >90 |

TABLE 2-continued

Reaction Yield of 1-S-3,5-bis(methoxycarbonyl)phenylene
N,N-dimethylthiocarbamate As a Function of Temperature
and Time

| Temperature, ° C. | Time, min | Yield, %[a] |
|---|---|---|
| 232 | 90 | 95 |
| 232–235 | 60 | 100 |
| 232–235 | 90 | 100 |
| 232–235 | 120 | 100 |

[a]The yields were determined by comparing the proton NMR signal intensities of the —N(CH$_3$)$_2$ groups of the starting material and the product.

The white solid first melted into a yellowish oil, then gradually became dark brown. After cooling to room temperature, a tar-like solid was obtained. Recrystallization from methanol gave 1-S-3,5-bis(methoxycarbonyl)phenylene N,N-dimethylthiocarbamate as a gray solid having the following characteristics: mp 117–118° C.; $^1$H NMR (in CDCl$_3$ w/TMS, ppm): 3.06 (s, 3H, NCH$_3$), 3.12 (s, 3H, NCH$_3$), 3.94 (s, 6H, OCH$_3$), 8.34 (s, 2H, CH), 8.69 (s, 1H, CH); {$^1$H}$^{13}$C NMR (in CDCl$_3$ w/TMS, ppm): 37.06 (N(CH$_3$)$_2$), 52.53 (OCH$_3$), 130.90 (C4), 131.44 (C3, C5), 131.58 (C2, C6), 140.87 (C1), 165.81 (COOR), 165.94 (SC(O)NR$_2$); $^1$H-$^{13}$C NMR (in CDCl$_3$ w/TMS, ppm): 37.06 (quartet, N(CH$_3$)$_2$, $^1J_{CH}$=139.6 Hz), 52.53 (quartet, OCH$_3$, $^1J_{CH}$=147.34 Hz), 130.90 (doublet of triplets, C4, $^1J_{CH}$=167.65 Hz, $^3J_{CH}$=6.448 Hz), 131.44 (C3, C5), 131.58 (doublet of doublets,. C2, C6, $^1J_{CH}$=168.3 Hz, $^3J_{CH}$=6.448 Hz), 140.87 (C1), 165.81 (COOR), 165.94 (SC(O)NR$_2$).

The 1-O-3,5-bis(methoxycarbonyl)phenylene N,N-dimethylthiocarbamate (112.2 g, 0.377 mol) was placed in a 2-L two-necked round-bottom flask equipped with a magnetic stirring bar, a condenser, and a thermometer. The flask was submerged in an oil bath preheated to 232–234° C. and kept at that temperature for 2 hours. The resulting dark brown oil was allowed to cool to about 80° C. Then the thermometer was replaced by a gas inlet tube, and the system was purged with nitrogen before 850 mL of 2.7 N NaOH was added. The mixture was heated under reflux for 2 hours, cooled to room temperature, and acidified to pH<4 with 10% aqueous HCl. Then the beige solid product was washed, preferably 3 times, with 400-mL portions of water and dried under vacuum at 60–70° C. to obtain 5-mercaptoisophthalic acid. Testing of the compound revealed the following properties: yield 67.5 g (90.3%); mp 240–246° C.; $^1$H NMR (in DMSO-d$_6$ w/TMS, ppm): 3.02 (s, 1H, SH), 8.24 (s, 2H, CH), 8.37 (s, 1H, CH), 13.50 (broad, 2H, COOH); {$^1$H}$^{13}$C NMR (in DMSO-d$_6$ w/TMS, ppm): 129.43 (C2), 130.88 (C4, C6), 134.74 (C1, C3), 136.51 (C5), 166.91 (COOH); $^1$H-$^{13}$C NMR (in DMSO-d$_6$w/TMS, ppm): 129.43 (d, C2, $^1J_{CH}$=167.39 Hz), 130.88 (d, C4, C6, $^1J_{CH}$=165.27 Hz), 134.74 (C1, C3), 136.51 (C5), 166.91 (COOH).

In the final step of the synthesis, to a 1-L round-bottom flask equipped with a magnetic stirring bar, a water separator, and a condenser were added 65.1 g (0.328 mol) of powdered 5-mercaptoisophthalic acid, 113 mL (94.2 g, 0.723 mol) of 2-ethyl-1-hexanol, 200 mL of benzene, and 4 mL of concentrated H$_2$SO$_4$. After the mixture had been heated under reflux for a sufficient time, approximately 3 h, about 12 mL (0.67 mol) of water had been collected by the water separator. The mixture was allowed to reflux until all of the solid was dissolved, generally about 24 hours, and a dark brown solution was obtained. After cooling to room temperature, the solution was poured into ice water, and the organic layer was washed in succession with 50 mL of saturated NaHCO$_3$ solution and two 50-mL portions of water. The organic layer was dried over anhydrous MgSO$_4$, and the dried solution was decolorized with ca. 10 g of activated carbon. After filtration, most of the benzene was removed by distillation at atmospheric pressure, and the excess 2-ethyl-1-hexanol and a trace amount of benzene were then removed by distillation at about 1 torr. The residual oil was bis(2-ethylhexyl) 5-mercaptoisophthalate. Testing on the compound revealed the following data: yield 132.7 g (95.5%); GC purity >89%; $^1$H NMR (in CDCl$_3$ w/TMS, ppm): 0.94 (m, 8H, CH$_2$), 1.40 (m, 20H, CH$_2$CH$_3$), 1.75 (m, 2 H, CH), 3.77 (s, 1H, SH), 4.28 (d, 4H, CH$_2$), 8.11 (s, 2H, CH), 8.43 (s, 1H, CH); {$^1$H}$^{13}$C NMR (in CDCl$_3$ w/TMS, ppm): 11.125 (C6'/C8'), 14.031 (C6'/C8'), 23.050 (C5'/C7'), 24.211 (C5'/C7'), 29.154 (C3'/C4'), 30.760 (C3'/C4'), 39.196 (C2'), 68.107 (C1'), 127.87 (C2), 132.23 (C1, C3), 133.09 (C5), 134.14 (C4, C6), 165.47 (COOR); GC-MS (in acetone): 422 (M$^+$).

The reaction sequence for the synthesis just described is as follows:

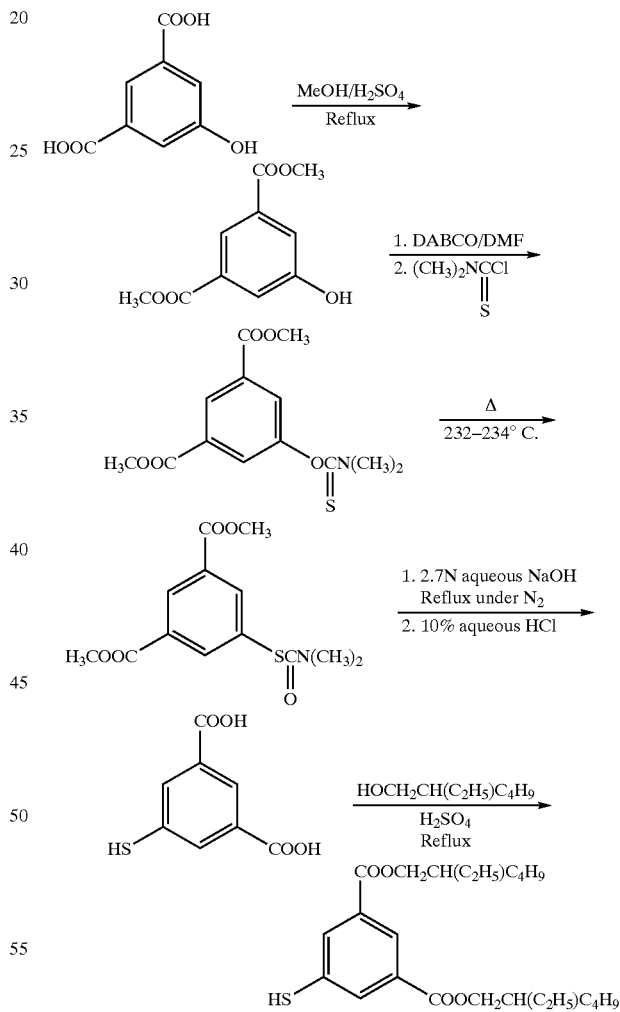

2-Ethylhexyl 3-mercaptobenzoate is a compound also disclosed by Formula I set forth hereinabove, wherein n=1, m=0, p=1, and R$^1$ is 2-ethylhexyl, with the sulfhydryl group being in a meta position. 2-Ethylhexyl 3-mercaptobenzoate and similar compounds can be prepared from carboxylic acids by utilizing a process including a chlorosulfonation step, a reduction step, and a subsequent esterification step. Following is the synthesis for 2-ethylhexyl 3-mercaptobenzoate.

Preparation of 3-Chlorosulfonylbenzoic Acid

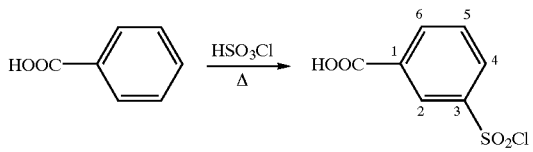

Benzoic acid (250 g, 2.05 mol) was placed in a 1-L round-bottom flask, and chlorosulfonic acid (1 L, 1760 g, 15.1 mol) was added. The mixture was heated with stirring at 120–125° C. for 2 h, allowed to cool to 40–50° C., and added dropwise to an excess of crushed ice. The precipitated product was collected by filtration and dissolved in 1 L of ethyl acetate; then the aqueous layer that formed was separated, and the organic layer was washed with 100 mL of water, dried over sodium sulfate, and concentrated by evaporation to near dryness. After trituration with 300 mL of hexane, the product was collected by filtration, washed on the filter with 200 mL of hexane, and dried in air to give 384.1 g (85%) of 3-chlorosulfonylbenzoic acid, mp 134–135° C. (lit. mp 134–135° C.); $^1$H NMR (400 MHz, in CDCl$_3$ w/TMS, ppm) 11.43 (broad s, CO$_2$$\underline{H}$), 7.81 (t, $\underline{J}$=8.0 Hz, H-5), 8.32 and 8.50 (2d, $\underline{J}$=8.0 Hz, H-4 and H-6), 8.79 (t, $\underline{J}$=1.6 Hz, H-2); {$^1$H}$^{13}$C NMR (100 MHz, in CDCl$_3$ w/TMS, ppm) 170.00 ($\underline{C}$=O), 145.06 (C-3), 136.71 (C-6), 131.92 (C-4), 131.31 (C-1), 130.63 (C-5), 128.91 (C-2).

Preparation of 3-Mercaptobenzoic Acid

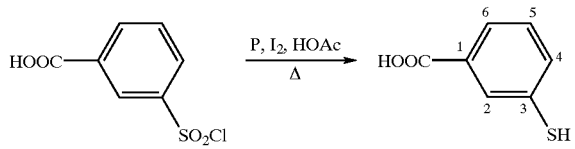

3-Chlorosulfonylbenzoic acid (156.0 g, 0.707 mol), acetic acid (240 mL), and red phosphorus (78.5 g, 2.53 mol) were placed in a 2-L three-neck flask. The mixture was heated to 110° C. and stirred while a solution of iodine (2.82 g, 0.011 mol) in acetic acid (66 mL) was added dropwise over about 30 min, so as to maintain the color of iodine vapor. The stirred mixture was cooled to 100° C. and treated dropwise with 41 mL (2.3 mol) of water over a 10-min period, then heated at reflux temperature for 1.5 h and subsequently cooled to 90° C. Following the addition of saturated sodium chloride solution (250 mL) and water (500 mL), the mixture was kept at 0–5° C. for 1 h and filtered. The damp filter cake was slurried with 450 mL of acetone, and the excess red phosphorus was removed by filtration; then the acetone was evaporated from the filtrate while adding 500 mL of water. The resultant solid was filtered off and dried under vacuum to give 100.1 g (92%) of 3-mercaptobenzoic acid, mp 138–141° C. (lit. mp 138–141° C.); $^1$H NMR (400 MHz, in CDCl$_3$ w/TMS, ppm) 3.59 (s, S$\underline{H}$), 7.36 (t, $\underline{J}$=7.8 Hz, H-5), 7.51 and 7.90 (2d, $\underline{J}$=7.8 Hz, H-4 and H-6), 8.03 (s, H-2); {$^1$H}$^{13}$C NMR (100 MHz, in CDCl$_3$ w/TMS, ppm) 171.77 ($\underline{C}$=O), 134.49 (C-4), 132.24 (C-1), 130.86 (C-2), 130.34 (C-3), 129.42 (C-5), 127.59 (C-6).

Preparation of 2-Ethylhexyl 3-Mercaptobenzoate

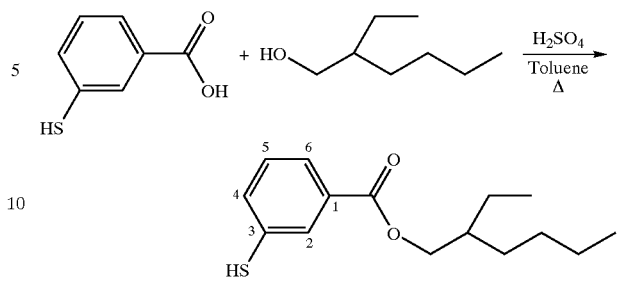

2-Ethyl-1-hexanol (44.4 g, 0.341 mol), 3-mercaptobenzoic acid (35.0 g, 0.227 mol), toluene (250 mL) (or other suitable solvent forming an azeotrope with water), and concentrated sulfuric acid (0.2 mL) were placed in a 500-mL three-neck round-bottom flask equipped with a magnetic stirring bar, a water separator, and a reflux condenser. After the mixture had been heated under reflux with stirring for 6 h, the solid 3-mercaptobenzoic acid had disappeared, and 4.14 mL (0.230 mol) of water had been collected by the water separator. The mixture was allowed to cool to room temperature and washed in succession with 20 mL of saturated NaHCO$_3$ solution and two 50-mL portions of brine. Then the organic layer was dried over anhydrous MgSO$_4$ and freed of solvent by rotary evaporation under vacuum to give 57.2 g (95%) of residual 2-ethylhexyl 3-mercaptobenzoate as a mobile straw-colored oil; $^1$H NMR (400 MHz, in CDCl$_3$ w/TMS, ppm) 0.89–0.97 (m, 6H, 2C$\underline{H}_3$), 1.30–1.48 (m, 8H, 4C$\underline{H}_2$), 1.67–1.76 (m, 1H, C$\underline{H}$), 3.56 (s, 1H, S$\underline{H}$), 4.19–4.27 (m, 2H, OC$\underline{H}_2$), 7.30 (t, $\underline{J}$=7.8 Hz, H-5), 7.43 and 7.81 (2d, $\underline{J}$=8.0 Hz, H-4 and H-6), 7.94 (t, $\underline{J}$=1.8 Hz, H-2); {$^1$H}$^{13}$C NMR (100 MHz, in CDCl$_3$ w/TMS, ppm) 166.17 ($\underline{C}$=O), 133.50 (C-4), 131.86 and 131.65 (C-1 and C-3), 130.29 (C-2), 129.24 (C-5), 126.91 (C-6), as well as 67.85, 39.21, 30.88, 29.33, 24.30, 23.32, 14.43, and 11.44 (8 aliphatic Cs).

Yet another aromatic compound containing ester functionality and at least one sulfhydryl group, which can be prepared from Formula I, is 2-ethylhexyl 2-mercaptobenzoate, wherein n=1, m=0, p=1, and R$^1$ is 2-ethythexyl, with the sulfhydryl group being in an ortho position. The method of preparation is as follows:

Preparation of 2-Ethylhexyl 2-Mercaptobenzoate

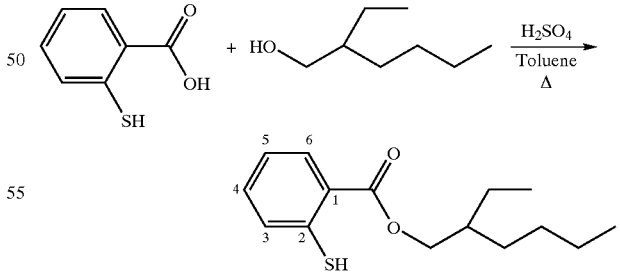

2-Ethyl-1-hexanol (21.0 g, 0.161 mol), 2-mercaptobenzoic acid (25.0 g, 0.162 mol), toluene (200 mL), and concentrated sulfuric acid (0.2 mL) were placed in a 500-mL three-neck round-bottom flask equipped with a magnetic stirring bar, a water separator, and a reflux condenser. After the mixture had been heated under reflux with stirring for 6 h, the solid 2-mercaptobenzoic acid had disappeared, and 2.90 mL (0.161 mol) of water had been collected by the water separator. The mixture was allowed to cool to room temperature and washed in succession with 20 mL of saturated NaHCO$_3$ solution and two 50-mL portions of brine. Then the organic layer was dried over anhydrous MgSO$_4$ and freed of solvent by rotary evaporation under vacuum to give 40.9 g (95%) of residual 2-ethylhexyl 2-mercaptobenzoate as a mobile straw-colored oil; $^1$H NMR (400 MHz, in CDCl$_3$ w/TMS, ppm) 0.88–0.97 (m, 6H, 2C$\underline{H}_3$), 1.3–1.5 (m, 8H, 4C$\underline{H}_2$), 1.68–1.78 (m, 1H, C$\underline{H}$), 4.21–4.29 (m, 2H, OC$\underline{H}_2$), 4.73 (s, 1H, S$\underline{H}$), 7.1–7.3 [m, 3H, H-4 and H-5 with d (J=3.2 Hz) for H-3 at 7.29], 8.01 (d, J=7.6 Hz, H-6); {$^1$H}$^{13}$C NMR (100 MHz, in CDCl$_3$ w/TMS, ppm) 166.99 ($\underline{C}$=O), 138.49 and 126.39 (C-1 and C-2), 132.53, 131.77, 131.12, and 124.82 (C-3, -4, -5, and -6), 67.86, 39.19, 30.92, 29.33, 24.34, 23.35, 14.44, and 11.46 (8 aliphatic Cs).

Aliphatic

In a further embodiment, the organic thiols of the present invention are aliphatic esters having at least one sulfhydryl group. The aliphatic ester thiol compounds can be derived from a mono- or polycarboxylic acid and can generally be described by the formulae:

  Formula IIA

  Formula IIB wherein R$^3$ and each R$^4$, independently, are straight chain or branched aliphatics, such as alkyls, having generally from 1 to about 20, and preferably from about 1 or 2 to about 10 carbon atoms, wherein y and z, independently, can be 0, 1, 2, to about 10 or more, wherein x is 1, 2, or an integer up to about 10. It is to be understood that all of the groups in brackets do not necessarily have the same structure in a given compound. That is, for example, if x is 2 or greater, one R$^4$ can independently have a different structure than another R$^4$, i.e. one R$^4$ can be propyl and another R$^4$ ethyl. Preferred aliphatic compounds include di-ester organic thiols wherein at least one sulfhydryl substituent is attached to an aliphatic group either between the ester functional groups (acyl portion of the ester) or external thereof (alkyl portion of the ester). General formulae for representative di-ester organic thiol compounds include the following:

Formula III

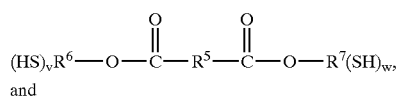

and

Formula IV

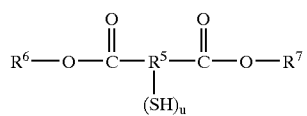

wherein R$^5$, R$^6$, and R$^7$, independently, are straight chain or branched aliphatics, such as alkyls, having from 1 to about 20 carbon atoms, and preferably from about 2 to about 10 carbon atoms, and u, v, and w, independently, are either 0, 1, or 2, or an integer up to about 10. Independent examples of R$^5$, R$^6$, and R$^7$ are 2-ethylhexyl, ethyl, ethylidene, butyl, butylidene, hexyl, hexylidene, decyl, and decylidene.

A few specific examples of compounds which can be formed from Formulae IIA, IIB, III, and IV are:

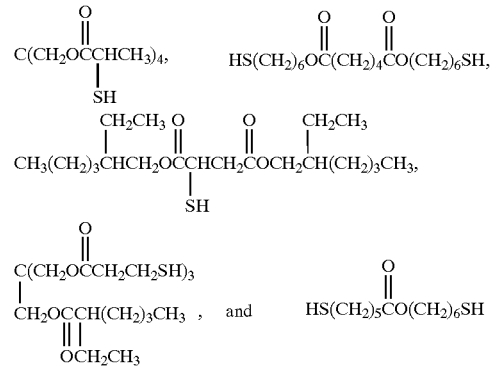

The numerous compounds described by Formulae IIA, IIB, III, and IV can be synthesized substantially as follows. A desired amount of a carboxylic acid or polycarboxylic acid which is optionally substituted with one or more sulfhydryl groups is added to a reaction vessel which is desirably equipped with a mechanical stirrer, a water separator, and a condenser. From about 0.1 to about 5 moles of an aliphatic alcohol or polyol optionally substituted with a sulfhydryl group is added to the reaction vessel per mole of carboxyl groups. Benzene, toluene, or other suitable entraining agent for water in an amount from about 0.2 to 2.0 liters per mole of carboxyl groups, and about 0.02 to about 0.2 moles per mole of carboxylic acid, of a strong acid, i.e., one having a concentrated pH of at least 1 to about 3, such as H$_2$SO$_4$, are added to the vessel. The mixture is heated under reflux with stirring, and the progress of the reaction can be followed by GC-MS analysis. After a period of time that depends upon the structures of the starting materials, the carboxylic acid disappears, and about 1 mole of water per mole of carboxyl groups has been collected by the water separator. Upon cooling to room temperature, the mixture is extracted with a quantity of saturated aqueous NaHCO$_3$ or Na$_2$CO$_3$ solution and washed with portions of water. The organic layer is dried over anhydrous MgSO$_4$ or other suitable drying agent, and most of the benzene is removed by rotary evaporation under aspirator vacuum at about 45–50° C. Trace amounts of residual benzene and excess aliphatic alcohol optionally sulfhydryl substituted are removed by vacuum distillation at elevated temperature and about 0.01 to about 5.0 mm pressure to yield an aliphatic ester thiol as described above.

As apparent from the above description, organic thiol compounds defined by at least Formula III can be formed by utilizing sulfhydryl group substituted aliphatic alcohols, and the organic thiol compounds of at least Formula IV can be formed by utilizing a sulfhydryl group substituted carboxylic diacid. Furthermore, compounds of Formulae IIA and IIB, wherein y and z are both positive integers, can be formed when both sulfhydryl substituted carboxylic acids or polyacids and sulfhydryl substituted aliphatic alcohols or polyols are utilized in the reaction.

Bis(6-mercaptohexyl) adipate

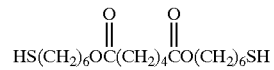

is an example of a compound disclosed by Formula III of the present invention, wherein R$^5$ is 1,4-butylidene, R$^6$ and R$^7$ are hexyl, and v and w are 1. The synthetic method for the preparation of bis(6-mercaptohexyl) adipate is as follows:

To a 1-liter round-bottom flask equipped with a magnetic stirring bar, a water separator, and a condenser were added 58.5 grams (0.400 mol) of powdered adipic acid, 110.7 grams (0.825 mol) of 6-mercapto-1-hexanol, 200 milliliters of benzene, and 1 milliliter (80 drops) of concentrated sulfuric acid. The mixture was heated under reflux with stirring, and the progress of the reaction was followed by GC-MS analysis. After 2–3 hours, the solid adipic acid had disappeared, and 15.8 milliliters (0.878 mol) of water had been collected by the water separator. Upon cooling to room temperature, the mixture was extracted with 60 milliliters of saturated NaHCO$_3$ solution and washed with two 100-milliliter portions of water. The organic layer was dried over anhydrous MgSO$_4$, and most of the benzene was removed by rotary evaporation under aspirator vacuum at 45–50° C. Trace amounts of residual benzene and 6-mercapto-1-hexanol then were removed by vacuum distillation at 160° C. (bath temperature) and 0.5 millimeter pressure to yield bis(6-mercaptohexyl) adipate as a straw-colored liquid. Yield of bis(6-mercaptohexyl) adipate, 123.6 grams (81.6%, calcd. 151.4 grams); GC purity, >95%; $^1$H NMR (in CDCl$_3$ w/TMS, ppm): 1.54 (t, 4H, C$\underline{H}_2$C$\underline{H}_2$CO$_2$R), 1.26–1.66 (br, 16H, OCH$_2$(CH$_2$)$_4$), 2.10 (t, 2H, S$\underline{H}$), 2.29 (t, 4H, C$\underline{H}_2$CO$_2$R), 2.47 (quartet, 4H, C$\underline{H}_2$S$\underline{H}$), 4.00 (t, 4H, OC$\underline{H}_2$); $\{^1H\}^{13}$C NMR (in CDCl$_3$ w/TMS, ppm): 24.32 (C3/C6), 24.38 (C3/C6), 25.33 (C3'), 27.83 (C2/C4), 28.42 (C2/C4), 33.73 (C5/C2'), 33.78 (C5/C2'), 64.08 (C1), 172.91 (C$\underline{O}_2$R).

Bis(2-ethylhexyl) mercaptosuccinate

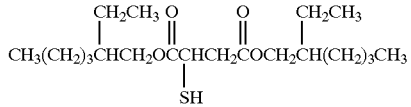

is an example of a compound disclosed by Formula IV of the present invention, wherein R$^5$ is 1,2-ethylidene, R$^6$ and R$^7$ are 2-ethylhexyl, and u is 1. The synthetic method for the preparation of bis(2-ethylhexyl) mercaptosuccinate is as follows:

To a 1-liter round-bottom flask equipped with a magnetic stirring bar, a water separator, and a condenser were added 75.0 grams (0.500 mol) of powdered mercaptosuccinic acid, 170.0 milliliters (141.6 grams, 1.087 mol) of 2-ethyl-1-hexanol, 250 milliliters of benzene, and 1 milliliter (80 drops) of concentrated sulfuric acid. The mixture was heated under reflux with stirring, and the progress of the reaction was followed by GC-MS analysis. After approximately 3 hours, the solid mercaptosuccinic acid had disappeared, and about 19 milliliters (1.1 mol) of water had been collected by the water separator. Refluxing was allowed to continue overnight in order to ensure completion of the esterification. Upon cooling to room temperature, the mixture was extracted with 50 milliliters of saturated NaHCO$_3$ solution and washed with two 100 milliliter portions of water. The organic layer was dried over anhydrous MgSO$_4$, and most of the benzene was removed by rotary evaporation under aspirator vacuum at 45–50° C. Trace amounts of residual benzene and 2-ethyl-1-hexanol then were removed by vacuum distillation at 140° C. (bath temperature) and 0.5 millimeter to yield bis(2-ethylhexyl) mercaptosuccinate as a straw-colored liquid. Yield of bis(2-ethylhexyl) mercaptosuccinate, 177.0 grams (94.5%, calcd. 187.3 grams); GC purity, >94%; $^1$H NMR (in CDCl$_3$ w/TMS, ppm): 0.87–0.92 (br, 12H, CH$_3$), 1.29–1.43 (br, 16H, CH$_2$), 1.54–1.64 (br, 2H, CH), 2.19 (d, 1H, S$\underline{H}$), 2.76 (d of d, 1H, C$\underline{H}_2$CO$_2$R), 3.02 (d of d, 1H, C$\underline{H}_2$CO$_2$R), 3.74–3.80 (d of quartet, 1H, C$\underline{H}$CH$_2$CO$_2$R), 4.00–4.14 (m, 4H, OCH$_2$); $\{^1H\}^{13}$C NMR (in CDCl$_3$ w/TMS, ppm): 10.93, 10.96, and 10.98 (C8), 14.03 (C6), 22.94 (C7), 23.70 (C5), 28.86 and 28.89 (C4), 30.25 and 30.30 (C3), 36.35 (C$\underline{S}$H), 38.68, 38.69, 38.73, and 38.75 (C2), 39.87 (C$\underline{H}_2$CO$_2$R), 67.30 and 67.94 (C1), 170.16 and 172.13 (C$\underline{O}_2$R).

Pentaerythritol tetrakis(2-mercaptopropionate)

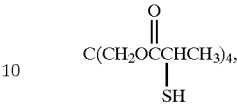

is an example of a compound disclosed by Formula IIB of the present invention, wherein R$^3$ is pentaerythrityl, R$^4$ is ethyl, x is 4, y is 1, and z is 0. The synthetic method for the preparation of pentaerythritol tetrakis(2-mercaptopropionate) is as follows:

To a 500-milliliter round-bottom flask equipped with a magnetic stirring bar, a water separator, and a condenser were added 27.23 grams (0.200 mol) of pentaerythritol, 90.22 grams (0.850 mol) of 2-mercaptopropionic acid, 100 milliliters of toluene, and 0.5 milliliter of concentrated sulfuric acid. The mixture was heated under reflux with stirring. After about 2 days, the solid material had disappeared, and about 17 milliliters (0.94 mol) of water had been collected by the water separator. Upon cooling to room temperature, the mixture was extracted with 30 milliliters of saturated NaHCO$_3$ solution and washed with two 50-milliliter portions of water. The organic layer was dried over anhydrous MgSO$_4$, and most of the toluene and residual 2-mercaptopropionic acid were removed by distillation under vacuum. Recrystallization of the residue from ethanol gave 86.0 grams (88.4%, calcd. 97.3 grams) of pentaerythritol tetrakis(2-mercaptopropionate) as a white solid, mp 93–96° C.; $^1$H NMR (in CDCl$_3$ w/TMS, ppm): 4.17–4.30 (AB m, 8H, C$\underline{H}_2$O), 3.50 (pentuplet, 4H, C$\underline{H}$SH), 2.17 (d of d, 4H, SH), 1.51 (d, 12H, C$\underline{H}_3$); $\{^1H\}^{13}$C NMR (in CDCl$_3$ w/TMS, ppm): 172.79 (C=O), 62.47 (C$\underline{H}_2$O), 43.05 [C(CH$_2$)$_4$], 35.43 (C$\underline{H}$SH), 20.94 (C$\underline{H}_3$).

A further pentaerythritol derivative, pentaerythritol 2-ethylhexanoate tris(2-mercaptopropionate):

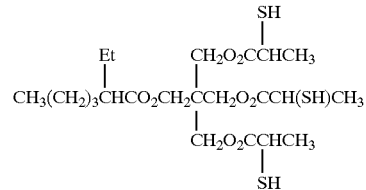

is disclosed by Formula IIB, wherein R$^3$ is pentaerythrityl, x is 4, R$^4$ is ethyl, ethyl, ethyl and 2-ethylhexyl, z is zero, and y is 3 with the sulfhydryl group pendant from the second carbon atom of each of the propionate groups of the compound. The synthetic method for the preparation of pentaerythritol 2-ethylhexanoate tris(2-mercaptopropionate) is as follows: Pentaerythritol (27.23 g, 0.200 mol), 2-mercaptopropionic acid (68.0 g, 0.641 mol), toluene (250 mL), and concentrated sulfuric acid (0.5 mL) were placed in a 1-L round-bottom flask equipped with a magnetic stirring bar, a water separator, and a condenser. The mixture was heated under reflux with stirring for 2 days; then 2-ethylhexanoic acid (29.0 g, 0.201 mol) and an additional amount (0.2 mL) of concentrated sulfuric acid were introduced. Following an additional day of stirring and heating, the total volume of water collected by the water separator was 17 mL (0.94 mol). The reaction mixture was allowed to cool to room temperature, then washed in succession with 40 mL of saturated NaHCO$_3$ solution and two 50-mL portions of brine. The organic layer was dried over anhydrous MgSO$_4$ and subjected to vacuum distillation at 130° C. in order to remove most of the toluene as well as any unconverted 2-mercaptopropionic acid and 2-ethylhexanoic acid. The residual pentaerythritol 2-ethylhexanoate tris(2-mercaptopropionate) (70.0 g; yield, 66.5%) was a straw-colored oil; $^1$H NMR (in CDCl$_3$ w/TMS, ppm): 4.1–4.3 (m, 8H, C$\underline{H}_2$O), 3.4–3.5 (m, 3H, C$\underline{H}$SH), 2.2–2.3 (m, 1H, C$\underline{H}$CO$_2$), 2.12 (d of d, 3H, S$\underline{H}$), 1.45–1.65 (m, 13H, HSCHC$\underline{H}_3$ and CC$\underline{H}_2$C), 1.2–1.45 (m, 4H, CC$\underline{H}_2$C), 0.85 (t, 6H, CH$_3$C$\underline{H}_2$).

A dipentaerythritol derivative, dipentaerythritol hexakis(3-mercaptopropionate):

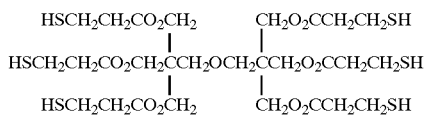

is disclosed by a variation of Formula IIB wherein dipentaerythrityl would be substituted for R$^3$, x is 6, each R$^4$ is ethyl, z is 0, and y is 6 with the sulfhydryl group attached to the terminal carbon atom of the propionate groups. Dipentaerythritol hexakis(3-mercaptopropionate) can be prepared as follows: Dipentaerythritol (25.5 g, 0.100 mol), 3-mercaptopropionic acid (74.3 g, 0.700 mol), toluene (250 mL), and concentrated sulfuric acid (0.5 mL) were placed in a 1-L round-bottom flask equipped with a magnetic stirring bar, a water separator, and a condenser. The mixture was heated under reflux with stirring for 2 days, then allowed to cool to room temperature and washed in succession with 20 mL of saturated NaHCO$_3$ solution and two 50-mL portions of brine. The organic layer was dried over anhydrous MgSO$_4$, and most of the toluene and any unconverted 3-mercaptopropionic acid were removed by vacuum distillation at 130° C. The residue, a viscous, colorless oil, was essentially pure dipentaerythritol hexakis(3-mercaptopropionate) (45.4 g; yield, 58.0%); $^1$H NMR (in CDCl$_3$ w/TMS, ppm): 4.09 (s, 12H, C$\underline{H}_2$OC=O), 3.38 (s, 4H, C$\underline{H}_2$OC$\underline{H}_2$), 2.7–2.75 (m, 12H, C$\underline{H}_2$SH), 2.63 (t, 12H, C$\underline{H}_2$C=O), 1.61 (t, 6H, S$\underline{H}$); {$^1$H}$^{13}$C NMR (in CDCl$_3$ w/TMS, ppm): 171.19 ($\underline{C}$=O), 69.86 ($\underline{C}$H$_2$OCH$_2$), 62.74 ($\underline{C}$H$_2$OC=O), 43.27 [$\underline{C}$(CH$_2$)$_4$], 38.57 ($\underline{C}$H$_2$C=O), 19.95 ($\underline{C}$H$_2$SH).

Di-Ester Ether Compounds Containing Sulfhydryl Groups

In yet another embodiment of the present invention, the organic thiols of the present invention are di-ester ether compounds having at least one sulfhydryl group attached thereto. The di-ester ether compounds can generally be described by the formula:

Formula V wherein R$^8$ and R$^9$, independently, comprise straight chain or branched alkylidenes having from 1 or about 2 to about 15 carbon atoms, and preferably from about 2 to about 10 carbon atoms, or an aromatic or a substituted aromatic having from about 6 to about 15 carbon atoms, such as when (R$^8$O)$_D$R$^9$ is derived from diphenyl ether; and wherein R$^{10}$ and R$^{11}$, independently, comprise straight chain or branched alkyls having from 1 or about 2 to about 15 carbon atoms, and preferably from 1 to about 10 carbon atoms, or an aromatic or a substituted aromatic having from about 6 to about 15 carbon atoms; and wherein A and B independently are either 0, 1, 2, 3, 4, 5, or 6; and wherein D is an integer from 1 to about 10, with 1, 2, or 3 preferred.

Examples of organic thiol compounds which can be formed from Formula V include:

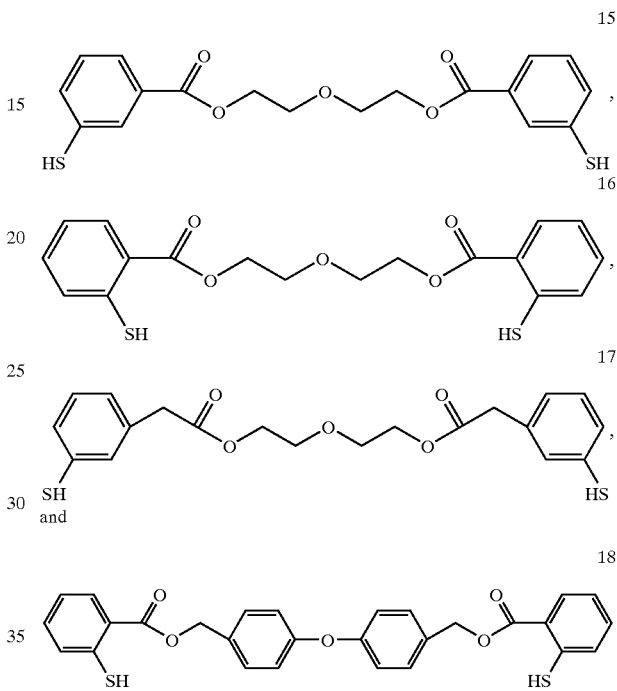

The preferred compounds of this embodiment can generally be prepared from ether diols and carboxylic acids containing at least one sulfhydryl group as follows. The ether diol (such as di(ethylene glycol) or tri(ethylene glycol)) and sulfhydryl-group-containing carboxylic acid are added to a reaction vessel in at least about a 1:2 mole ratio, respectively. Toluene or other suitable solvent that forms an azeotrope with water in an amount from about 1 to about 10 liters per mole of ether diol and a catalytic amount of a strong acid such as sulfuric acid, phosphoric acid, hydrochloric acid, or the like are also added to the reaction vessel, which is equipped with a stirring device, a water separator, and a reflux condenser. The mixture is heated under reflux at the boiling temperature of the solvent until the solid components dissolve or the reaction is complete, generally for a suitable length of time such as about six hours. Water is collected in the water separator. The mixture is cooled to room temperature, washed in succession first with an aqueous solution of NaHCO$_3$ or other weak base, then with brine, and dried over MgSO$_4$ or other suitable drying agent. Then the desired di-ester ether thiol is obtained as a residue after evaporation or distillation of the solvent.

Di(ethylene glycol) bis(3-mercaptobenzoate) (compound 15) is a compound which can be prepared from the above general formula and procedure, wherein R$^8$ and R$^9$ are each CH$_2$CH$_2$, R$^{10}$ and R$^{11}$ are each a benzene ring, and A and B are 1, wherein the sulfhydryl groups are attached to the benzene ring in a meta position, and D is 1. Di(ethylene glycol) bis(3-mercaptobenzoate) can be prepared as follows:

Di(ethylene glycol) (19.0 g, 0.179 mol), 3-mercaptobenzoic acid (57.9 g, 0.376 mol), toluene (250 mL), and concentrated sulfuric acid (0.2 mL) were placed in a 500-mL three-neck round-bottom flask equipped with a magnetic stirring bar, a water separator, and a reflux condenser. After the mixture had been heated under reflux with stirring for 6 h, the solid 3-mercaptobenzoic acid had disappeared, and 6.50 mL (0.361 mol) of water had been collected by the water separator. The mixture was allowed to cool to room temperature and washed in succession with 20 mL of saturated $NaHCO_3$ solution and two 50-mL portions of brine. Then the organic layer was dried over anhydrous $MgSO_4$ and freed of solvent by rotary evaporation under vacuum to give 67.4 g (99%) of residual di(ethylene glycol) bis(3-mercaptobenzoate) as a viscous straw-colored oil; $^1H$ NMR (400 MHz, in $CDCl_3$ w/TMS, ppm) 3.56 (s, 2H, 2S$\underline{H}$), 3.87 (t, J=4.6 Hz, 4H, C$\underline{H}_2$OC$\underline{H}_2$), 4.49 (t, J=4.6 Hz, 4H, 2C$\underline{H}_2O_2$C), 7.26 (t, J=8.0 Hz, H-5), 7.42 and 7.79 (2d, J=7.6 Hz, H-4 and H-6), 7.92 (s, H-2); $\{^1H\}^{13}C$ NMR (100 MHz, in $CDCl_3$w/TMS, ppm) 165.98 ($\underline{C}$=O), 133.67 (C-4), 131.98 (C-1), 131.03 (C-3), 130.36 (C-2), 129.26 (C-5), 127.02 (C-6), 69.38 ($\underline{C}H_2O\underline{C}H_2$), 64.44 (2$\underline{C}H_2O_2$C).

Di(ethylene glycol) bis(2-mercaptobenzoate) (compound 16) is another compound which can be prepared from the above general formula and procedure, wherein $R^8$ and $R^9$ are each $CH_2CH_2$, $R^{10}$ and $R^{11}$ are each a benzene ring, and A and B are 1, wherein the sulfhydryl groups are in an ortho position, and D is 1. Di(ethylene glycol) bis(2-mercaptobenzoate) can be prepared as follows:

Di(ethylene glycol) (20.0 g, 0.189 mol), 2-mercaptobenzoic acid (58.6 g, 0.380 mol), toluene (250 mL), and concentrated sulfuric acid (0.3 mL) were placed in a 500-mL three-neck round-bottom flask equipped with a magnetic stirring bar, a water separator, and a reflux condenser. After the mixture had been heated under reflux with stirring for 6 h, the solid 2-mercaptobenzoic acid had disappeared, and 7.5 mL (0.416 mol) of water had been collected by the water separator. The mixture was allowed to cool to room temperature and washed in succession with 20 mL of saturated $NaHCO_3$ solution and two 50-mL portions of brine. Then the organic layer was dried over anhydrous $MgSO_4$ and freed of solvent by rotary evaporation under vacuum to give 71.5 g (100%) of residual di(ethylene glycol) bis(2-mercaptobenzoate) as a viscous straw-colored oil; $^1H$ NMR (400 MHz, in $CDCl_3$ w/TMS, ppm) 3.86 (t, J=4.6 Hz, 4H, C$\underline{H}_2$OC$\underline{H}_2$), 4.48 (t, J=4.6 Hz, 4H, 2C$\underline{H}_2O_2$C), 4.65 (s, 2H, 2S$\underline{H}$), 7.0–7.3 [m, H-4 and H-5 with d (J=3.6 Hz) for H-3 at 7.26], 8.00 (d, J=7.6 Hz, H-6); $\{^1H\}^{13}C$ NMR (100 MHz, in $CDCl_3$ w/TMS, ppm) 166.69 ($\underline{C}$=O), 138.48 and 125.90 (C-1 and C-2), 132.76, 132.01, 131.07, and 124.89 (C-3, -4, -5, and -6), 69.31 ($\underline{C}H_2O\underline{C}H_2$), 64.49 (2$\underline{C}H_2O_2$C).

Mercaptophenylcarboxylates

In a further embodiment of the present invention, the organic thiols are mercaptophenylcarboxylates, preferably formed as a reaction product of a mercaptophenylcarboxylic acid and an alcohol. In a preferred embodiment, the alcohol is a polyol of di- or greater functionality. It is further preferred in one embodiment that the alcohol contain at least one ether group. The reaction products are synthesized in a few steps by a preferred route set forth herein. The organic thiols are utilized preferably as heat stabilizers in compositions containing chlorine- or bromine-containing polymers, such as but not limited to poly(vinyl chloride), which are substantially free and preferably free of metal-containing stabilizers, Lewis acids, and terpenes. The thiols are highly effective as primary thermal stabilizers and in further embodiments are excellent plasticizers when used at relatively high plasticizer loading levels as known in the art.

The mercaptophenylcarboxylic acids of the invention are carboxylic acids having a pendant mercaptophenyl group. The mercaptophenylcarboxylic acids are set forth by the formula:

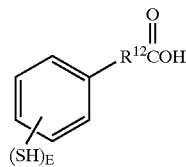

wherein $R^{12}$ is a straight chain or branched alkylene having from 1 to about 15 carbon atoms, with 1 to about 6 carbon atoms preferred, and wherein E is 1 to about 4 or 5. The sulfhydryl (mercapto) group is present in an ortho, meta, or para position, or optionally a combination thereof if more than one such group is present. Examples of mercaptophenylcarboxylic acids include, but are not limited to, 2-mercaptophenylacetic acid, 3-mercaptophenylacetic acid, 4-mercaptophenylacetic acid, 3,4-dimercaptophenylacetic acid, 2-(4-mercaptophenyl)propionic acid, 2-(3-mercaptophenyl)propionic acid, 3-(4-mercaptophenyl)propionic acid, and 2-(3-mercaptophenyl)butyric acid, and combinations thereof.

The alcohols utilized in the reaction are capable of undergoing an esterification reaction with the mercaptophenylcarboxylic acid. Suitable alcohols are mono-, di- and polyhydric alcohols, or mixtures thereof. The alcohols are described by the formula $R^{13}(OH)_f$, wherein f ranges from 1 to about 10, and preferably is 2 or 3 to about 4 or about 6, and wherein $R^{13}$ is i) a linear, cyclo-, or branched alkyl or alkylene group having from 1 to about 25 carbon atoms, and preferably from 2 or 3 to about 15 or 20 carbon atoms, or ii) an aralkyl or aralkylene group having from 7 to about 25 carbon atoms, with $R^{13}$ optionally containing heteroatoms such as an ethereal oxygen. In one embodiment, the alcohols are polyols of di- or greater functionality. In a preferred embodiment, the polyol contains one or more ether groups. Examples of alcohols include, but are not limited to, polyether polyols such as di(ethylene glycol) and tri(ethylene glycol), propanediol, butanediol, pentaerythritol, glycerol, 4,4'-dimethyloldiphenyl ether, and o-, m-, or p-xylene-α, α'-diol. Preferred alcohols are di(ethylene glycol), tri(ethylene glycol), and 1,3-propanediol. When f is 2 or more, alkylene or aralkylene is the proper term for the $R^{13}$ group.

The mercaptophenylcarboxylate organic thiols of this embodiment are described by the formula:

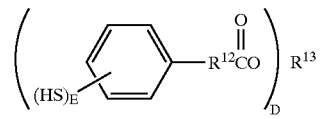

wherein E, $R^{12}$, and $R^{13}$ are defined hereinabove, and wherein D is 1 or 2 to about 10, and preferably 2 or 3 to about 4 or about 6.

Specific examples of mercaptophenylcarboxylate organic thiols are:

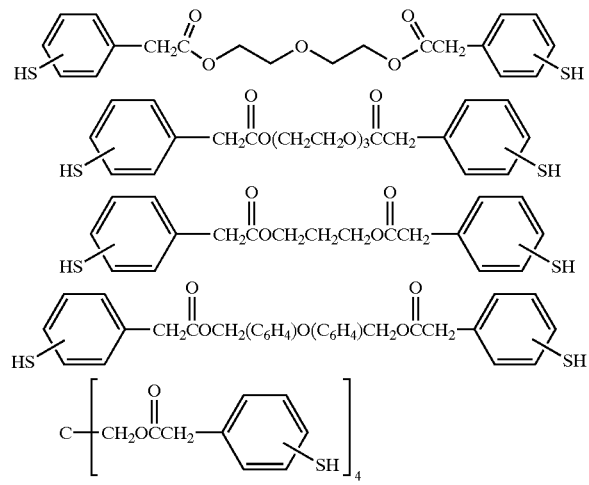

A method for synthesizing the mercaptophenylcarboxylate organic thiols of the invention is set forth below.

In one step, a mercaptophenylcarboxylic acid is prepared, preferably from the following general procedure. Chlorosulfonic acid is added, preferably dropwise, to a reaction vessel containing a phenylcarboxylic acid. The reaction vessel is preferably equipped with a mechanical stirrer or other agitation means. About 2 to about 20 mols of chlorosulfonic acid are utilized per mol of phenylcarboxylic acid while maintaining the temperature of the reaction mixture at about 0° C. plus or minus about 10° C. The mixture is allowed to warm to room temperature over an extended period of time, such as about 12 hours, and then added, preferably dropwise, to an excess of crushed ice in order to precipitate the mercaptophenylcarboxylic acid. The mercaptophenylcarboxylic acid is collected by suction filtration and dissolved in a solvent such as ethyl acetate. The organic layer is separated from the aqueous layer and washed with a quantity of water, subsequently dried over a suitable drying agent such as anhydrous sodium sulfate, and then evaporated to yield chlorosulfonylphenylcarboxylic acid. Often, an isomeric mixture is formed. If desired, the individual isomers can be isolated from this mixture by utilizing conventional separation techniques such as recrystallization or column chromatography.

In a next step, to form the mercaptophenylcarboxylic acid, the product from the above reaction is added to a reaction vessel along with about 1 to about 5 mols of red phosphorus, and the mixture is maintained at a temperature of about 90° C. to about 120° C. while a solution of a catalytic amount of iodine in acetic acid is added dropwise under agitation. After cooling to about 90° C. to 100° C., the stirred mixture is treated dropwise with a quantity of water over a period of time, such as about 10 minutes; heated under reflux for a period of time, such as about 1.5 hours; cooled to about 0° C. to about 10° C. for a period of time such as about 1 hour; and treated with additional water. The resultant solid mercaptophenylcarboxylic acid or mixture of the isomers thereof is then collected and optionally purified, recrystallized, decolorized, or a combination thereof.

An alternative route for forming the mercaptophenylcarboxylic acid can also be utilized. In this route, reactants such as red phosphorus and iodine are added to a reaction vessel along with the carboxylic acid, and the mixture is heated under reflux, preferably with agitation. A solution of chlorosulfonylphenylacetic acid(s) dissolved in a suitable solvent such as acetic acid is added slowly over a predetermined time period. After the addition is complete, the mixture is heated, preferably under agitation at about 90° C. to about 110° C. for a period of time, such as about 4 hours. Afterwards, the mixture is maintained at temperature while water is added thereto over a period of time, such as about 2 hours. The mixture is cooled to about minus 5° C. to about 0° C., and the unchanged phosphorus is removed by suction filtration. An additional quantity of water is added. The amount depends on the amounts of the starting materials. Thereafter, the desired product(s), mercaptophenylcarboxylic acid(s), is/are extracted with, for example, dichloromethane. The dichloromethane solution is subsequently dried with a suitable drying agent and evaporated to isolate the product.

To form the mercaptophenylcarboxylate, to a reaction vessel is/are added the mercaptophenylcarboxylic acid(s) and an alcohol in stoichiometric quantities to produce the desired end product, along with a strong acid such as sulfuric acid and a solvent, such as toluene. The reaction vessel is preferably equipped with an agitation means, a water separator, and a condenser. The mixture is heated under reflux for an extended period of time, such as about 6 hours or otherwise until the reaction is complete. After cooling to room temperature, the mixture is preferably washed with aqueous $NaHCO_3$ solution and portions of brine, then dried, preferably over $MgSO_4$ or other suitable drying agent. The reaction product(s), mercaptophenylcarboxylate(s), is/are isolated as known in the art, such as by dissolution in a solvent such as dichloromethane followed by treatment of the solution at the boiling point with a small amount of decolorizing carbon, hot filtration, and rotary evaporation to remove the solvent. If desired, the product can be purified by conventional methods such as column chromatography or recrystallization.

One suitable mercaptophenylcarboxylic acid which is reacted with an alcohol to form the mercaptophenylcarboxylate organic thiols of the present embodiment is mercaptophenylacetic acid, specifically the 3- and 4-isomers thereof. Mercaptophenylacetic acid can be prepared as follows. Chlorosulfonic acid (1 L, 1760 g, 15.10 mol) was added dropwise with stirring at 0±5° C. to a round-bottom flask containing 300.0 g (2.20 mol) of phenylacetic acid. The mixture was allowed to warm to room temperature overnight and then added dropwise to an excess of crushed ice, in order to precipitate the crude product, which was collected by suction filtration and dissolved in 750 mL of ethyl acetate. After separation of the aqueous layer that formed, the organic layer was washed with 100 mL of water, dried over anhydrous sodium sulfate, and evaporated nearly to dryness. The resultant solid was recovered by suction filtration and dried in air to obtain 440.9 g of product that yielded 160.0 g (31%) of a solid that melted at 129–130° C. after recrystallization from chloroform. This solid was shown by NMR analyses to consist primarily of 4-chlorosulfonylphenylacetic acid. Evaporation of the mother liquor left 280.9 g (yield, 54%) of material that was shown by NMR analyses to be mostly a 65:35 mixture of the 4- and 3- isomers, respectively, of the chlorosulfonyl product. Products having different isomer ratios were obtained from other runs. For a typical isomer mixture, $^1H$ NMR (in $CDCl_3$ w/TMS, ppm): 3.81 (s, 2H, $CH_2$), 7.41–8.02 (m, 4H, aromatic CH), 9.90 (broad s, 1H, $CO_2H$). For the essentially pure 4-isomer, $^1H$ NMR (in $CDCl_3$ w/TMS, ppm): 3.81 (s, 2H, $CH_2$), 7.56 (d, J=8.4 Hz, 2H, CH-2,6), 8.02 (d, J=8.4 Hz, 2H, CH-3,5), 8.47 (broad s, 1H, $CO_2H$); $\{^1H\}^{13}C$ NMR (in $CDCl_3$ w/TMS, ppm): 41.08 (CH$_2$), 127.54 (C-3,5), 131.03 (C-2,6), 141.33 (C-1), 143.54 (C-4), 176.15 (C=O). For the 3-isomer in a typical mixture, {$^1$H}$^{13}$C NMR (in CDCl$_3$ w/TMS, ppm): 40.31 (CH$_2$), 125.82 (C-4), 127.61 (C-2), 129.83 (C-5), 135.21 (C-1), 136.26 (C-6), 144.33 (C-3), 176.20 (C=O).

Two modifications of the same general method were used to form the mercaptophenylacetic acid. They afforded comparable yields, and both were applicable to chlorosulfonyl starting materials with various isomer compositions.

Modification A. A mixture of chlorosulfonylphenylacetic acids (130.0 g, 0.554 mol) containing a large preponderance of the 4-isomer, acetic acid (190 mL), and red phosphorus (50.0 g, 1.61 mol) was prepared in a round-bottom flask and kept at 110° C. while a solution of iodine (2.30 g, 9.06 mmol) in acetic acid (66 mL) was added dropwise with efficient mechanical stirring during 30 min (this procedure was designed to maintain the color of iodine vapor in the reaction vessel). After cooling to 100° C., the stirred mixture was treated dropwise with water (34 mL) during 10 min, heated under reflux for 1.5 h, kept at 0–5° C. for 1 h, and treated with an additional 500 mL of water. The resultant solid was collected by suction filtration and slurried with dichloromethane (200 mL); then the mixture was filtered with suction to remove the residual phosphorus and treated at the boiling point with a small amount of decolorizing carbon. Hot filtration and removal of the solvent by rotary evaporation afforded 78.7 g (yield, 84%) of a pale yellow solid, mp 79–84° C., that was shown by $^1$H and $^{13}$C NMR analyses to consist primarily of an 80:20 mixture of 4- and 3-mercaptophenylacetic acids, respectively.

Modification B. A mixture of red phosphorus (100.0 g, 3.23 mol), iodine (3.60 g, 14.2 mmol), and acetic acid (300 mL) contained in a round-bottom flask was heated under reflux with stirring while a solution of chlorosulfonylphenylacetic acids (mostly the 3- and 4-isomers, 200.0 g, 0.852 mol) in acetic acid (100 mL) was slowly added dropwise, so as to minimize the loss of iodine vapor. When the addition was complete, the stirred mixture was heated at 100° C. for 4 h, treated carefully (by slow addition) with water (72 mL), kept at 100° C. for an additional 2 h, and then cooled to minus 5 to about 0° C. Following the removal of unchanged phosphorus by suction filtration, an additional 500 mL of water was added, and the desired product was removed by extracting the mixture with two 200-mL portions of dichloromethane. The combined extracts were dried over anhydrous Na$_2$SO$_4$ and subjected to rotary evaporation to obtain 120.0 g (yield, 84%) of residual mercaptophenylacetic acid, mp 60–70° C., which was shown by NMR measurements to be mostly a mixture of the 4- and 3-isomers in a ratio of 55:45, respectively.

For the 4-isomer, $^1$H NMR (in CDCl$_3$ w/TMS, ppm): 3.44 (s, 1H, SH), 3.58 (s, 2H, CH$_2$), 7.14 (d, J=8.4 Hz, 2H, CH-3,5), 7.23 (d, J=8.4 Hz, 2H, CH-2,6), 11.10 (broad s, 1H, OH); {$^1$H}$^{13}$C NMR (in CDCl$_3$ w/TMS, ppm): 40.78 (CH$_2$), 129.89 and 130.36 (C-3,5 and C-2,6), 130.15 (C-4), 130.95 (C-1), 178.24 (C=O). For the 3-isomer, $^1$H NMR (in CDCl$_3$ w/TMS, ppm): 3.46 (s, 1H, SH), 3.57 (s, 2H, CH$_2$), 7.04–7.25 (m, 4H, aromatic CH), 11.10 (broad s, 1H, OH); {$^1$H}$^{13}$C NMR (in CDCl$_3$ w/TMS, ppm): 41.11 (CH$_2$), 126.96 (C-6), 128.56 (C-4), 129.54 (C-5), 130.41 (C-2), 131.55 (C-3), 134.39 (C-1), 177.82 (C=O).

In one embodiment, the mercaptophenylcarboxylate pentaerythritol tetrakis(3- and 4-mercaptophenylacetate),

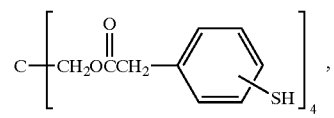

is prepared as follows.

Pentaerythritol (10.0 g, 0.0734 mol), a mixture of mercaptophenylacetic acids (62.0 g, 0.369 mol) containing ca. 80% of the 4-isomer, concentrated sulfuric acid (0.3 mL), and toluene (250 mL) were placed in a round-bottom flask equipped with a magnetic stirring bar, a water separator, and a condenser. During 6 h of heating under reflux with stirring, the solid organic acid mixture disappeared, and 7.5 mL (0.416 mol) of water was collected by the water separator. The mixture was allowed to cool to room temperature and washed in succession with 20 mL of saturated NaHCO$_3$ solution and two 50-mL portions of brine. Drying of the organic layer over anhydrous MgSO$_4$, followed by rotary evaporation and subsequent drying of the residue in a vacuum oven, afforded 51.3 g (yield, 95%) of a pale yellow solid mixture of pentaerythritol tetrakis (mercaptophenylacetate)s whose major isomeric constituent (ca. 80%) was shown to be the 4-one by NMR measurements: $^1$H NMR (in CDCl$_3$ w/TMS, ppm): 3.44–3.53 (m, 3H, SH and CH$_2$C=O), 3.92–3.99 (m with strong s at 3.92, 2H, CH$_2$O), 7.02–7.41 (m, 4H, aromatic CH); {$^1$H}$^{13}$C NMR (in CDCl$_3$ w/TMS, ppm): 40.35 (4-isomer CH$_2$C=O) and 40.69 (3-isomer CH$_2$C=O); 42.05 [C(CH$_2$)$_4$]; 61.96 and 61.98 (3- and 4-isomer CH$_2$O); 126.32, 127.61, 129.16, 129.45, 129.71, 129.80, 130.63, 132.31, 134.18, and 135.80 (aromatic C); 170.20 (3-isomer C=O) and 170.31 (4-isomer C=O).

An analogous preparation was carried out by starting with a 50:50 mixture of 3- and 4-mercaptophenylacetic acids. In this case, the crude product was dissolved in 400 mL of dichloromethane, and the solution was treated at the boiling point with a small amount of decolorizing carbon. Subsequent hot filtration, followed by rotary evaporation of the solvent, gave 52.5 g (yield, 97%) of a viscous pale yellow oil that was shown by NMR measurements to be pentaerythritol tetrakis(mercaptophenylacetate) containing equal amounts of the 3- and 4-isomers: $^1$H NMR (in CDCl$_3$ w/TMS, ppm): 3.45–3.56 (m, 3H, SH and CH$_2$C=O), 3.90–3.98 (m with strong s at 3.91, 2H, CH$_2$O), 6.95–7.40 (m, 4H, aromatic CH); {$^1$H}$^{13}$C NMR (in CDCl$_3$ w/TMS, ppm): 40.77 (4-isomer CH$_2$C=O) and 41.12 (3-isomer CH$_2$C=O); 42.50 [C(CH$_2$)$_4$]; 62.40 (CH$_2$O); 126.75, 128.45, 129.60, 129.88, 130.15, 130.20, 131.07, 131.71, and 134.63 (aromatic C); 170.55 (3-isomer C=O) and 170.78 (4-isomer C=O).

In a further embodiment, the mercaptophenylcarboxylate di(ethylene glycol) bis(3- and 4-mercaptophenylacetate),

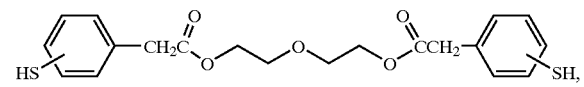

is prepared as follows.

A 55:45 mixture of the respective 4- and 3-mercaptophenylacetic acids (40.39 g, 0.240 mol), di(ethylene glycol) (12.00 g, 0.113 mol), concentrated sulfuric acid (0.2 mL), and toluene (200 mL) were placed in a round-bottom flask equipped with a magnetic stirring bar, a water separator, and a condenser. During 6 h of heating under reflux with stirring, the solid organic acid isomers disappeared, and 3.96 mL (0.220 mol) of water was collected by the water separator. The mixture was washed in succession with 20 mL of saturated NaHCO$_3$ solution and two 50-mL portions of brine, then dried over anhydrous MgSO$_4$ and freed of solvent on a rotary evaporator. Dissolution of the residue in 100 mL of dichloromethane, followed by treatment of the solution at the boiling point with a small amount of decolorizing carbon, hot filtration, and rotary evaporation to remove solvent, gave 42.0 g (yield, 91%) of a viscous pale yellow oil that was shown by NMR analyses to be di(ethylene glycol) bis(mercaptophenylacetate) containing the 4- and 3-isomers in a ratio of ca. 55:45, respectively: $^1$H NMR (in CDCl$_3$ w/TMS, ppm): 3.47 (s, 4-isomer SH) and 3.49 (s, 3-isomer SH), 1H in toto; 3.57–3.70 (m, 4H, CH$_2$C=O and CH$_2$OCH$_2$); 4.21–4.29 (m, 2H, CH$_2$OC=O); 7.08–7.47 (m, 4H, aromatic CH); {$^1$H}$^{13}$C NMR (in CDCl$_3$ w/TMS, ppm): 40.45 (4-isomer CH$_2$C=O); 40.78 (3-isomer CH$_2$C=O); 63.78, 63.80, and 63.85 (CH$_2$OC=O); 68.77 (CH$_2$OCH$_2$); 126.41, 127.83, 129.02, 129.08, 129.38, 129.81, 129.84, 131.00, 131.14, and 134.63 (aromatic C); 170.81 (3-isomer C=O) and 171.02 (4-isomer C=O).

In yet another embodiment, the mercaptophenylcarboxylate tri(ethylene glycol) bis(3- and 4-mercaptophenylacetate),

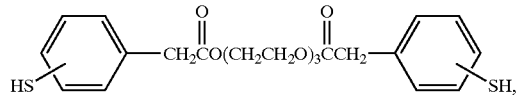

is prepared as follows.

A 55:45 mixture of the respective 4- and 3-mercaptophenylacetic acid isomers (40.0 g, 0.238 mol), tri(ethylene glycol) (15.0 g, 0.100 mol), concentrated sulfuric acid (0.2 mL), and toluene (200 mL) were placed in a round-bottom flask equipped with a magnetic stirring bar, a water separator, and a condenser. Heating of the mixture under reflux with stirring for 6 h led to the disappearance of the solid organic acid isomers and to the collection of 3.96 mL (0.220 mol) of water by the water separator. After cooling to room temperature, the mixture was washed in succession with 20 mL of saturated NaHCO$_3$ solution and two 50-mL portions of brine, then dried over anhydrous MgSO$_4$ and freed of solvent on a rotary evaporator. Dissolution of the residue in 400 mL of dichloromethane, followed by treatment of the solution at the boiling point with a small amount of decolorizing carbon, hot filtration, and rotary evaporation to remove solvent, gave 44.0 g (yield, 98%) of tri(ethylene glycol) bis(mercaptophenyl acetate) as a viscous pale yellow oil that was shown by NMR measurements to contain the 4- and 3-isomers in a ratio of ca. 55:45, respectively: $^1$H NMR (in CDCl$_3$ w/TMS, ppm): 3.44 (s, 4-isomer SH) and 3.47 (s, 3-isomer SH), 1H in toto; 3.56–3.66 (m, 6H, CH$_2$C=O and CH$_2$OCH$_2$); 4.23–4.26 (m, 2H, CH$_2$OC=O); 7.05–7.44 (m, 4H, aromatic CH); {$^1$H}$^{13}$C NMR (in CDCl$_3$ w/TMS, ppm): 40.91 (4-isomer CH$_2$C=O) and 41.24 (3-isomer CH$_2$C=O); 64.34 (CH$_2$OC=O); 69.34 (CH$_2$CH$_2$O$_2$C); 70.82 (CH$_2$OCH$_2$CH$_2$O$_2$C); 126.20–135.12 (at least 12 peaks, aromatic C); 171.29 (3-isomer C=O) and 171.50 (4-isomer C=O).

In a further embodiment, the mercaptophenylcarboxylate 1,3-propanediol bis(3- and 4-mercaptophenylacetate),

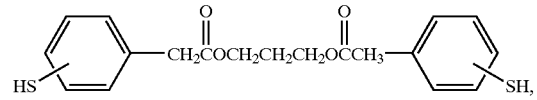

is prepared as follows.

1,3-Propanediol (9.50 g, 0.125 mol), a 55:45 mixture of the respective 4- and 3- isomers of mercaptophenylacetic acid (45.00 g, 0.268 mol), concentrated sulfuric acid (0.2 mL), and toluene (200 mL) were combined in a round-bottom flask equipped with a magnetic stirring bar, a water separator, and a condenser. During 6 h of heating under reflux with stirring, the solid organic acid isomers disappeared, and 4.46 mL (0.248 mol) of water was collected by the water separator. The mixture was allowed to cool to room temperature, washed in succession with 20 mL of saturated NaHCO$_3$ solution and two 50-mL portions of brine, then dried over anhydrous MgSO$_4$ and freed of solvent on a rotary evaporator. Dissolution of the residue in 400 mL of dichloromethane, followed by treatment at the boiling point with a small amount of decolorizing carbon, hot filtration, and rotary evaporation to remove solvent, gave 46.4 g (yield, 99%) of 1,3-propanediol bis(mercaptophenylacetate) as a viscous pale yellow oil that was shown by NMR analyses to contain the 4- and 3-isomers in a ratio of ca. 55:45, respectively: $^1$H NMR (in CDCl$_3$ w/TMS, ppm): 1.91–1.96 (m, 2H, CH$_2$CH$_2$CH$_2$); 3.44 (s, 4-isomer SH) and 3.47 (s, 3-isomer SH), 2H in toto; 3.53–3.63 (m, 4H, CH$_2$C=O); 4.10–4.14 (m, 4H, CH$_2$O); 7.03–7.44 (m, 8H, aromatic CH); {$^1$H}$^{13}$C NMR (in CDCl$_3$ w/TMS, ppm): 28.14 (CH$_2$CH$_2$CH$_2$); 40.99 (4-isomer CH$_2$C=O) and 41.31 (3-isomer CH$_2$C=O); 61.64 (CH$_2$O); 126.80–132.36 (at least 9 peaks, aromatic C); 171.20 (3-isomer C=O) and 171.41 (4-isomer C=O).

The organic thiol compounds disclosed by the present invention are used as additives for polymeric compounds, wherein, for example, the organic thiols can serve as plasticizers and/or stabilizers. The organic thiols are free of metal, and desirably are not used in conjunction with any metal-based stabilizers, Lewis acids, or terpenes. By metal-based stabilizers it is meant any metal compound, salt, complex, or the like of any of the metals, including the transition metals and rare earth, as set forth in groups 1–7 of the periodic table, such as, but not limited to the heavy metals, for example cadmium, mercury, lead, and the like as well as other generally environmentally unfriendly or undesirable compounds.

Examples of specific metal-based stabilizers which are avoided include those set forth in European Patent Application EP 0 945 484 A1 at least on page 3 thereof. Accordingly, the polymer compositions of the present invention are substantially free of the various metal-based stabilizers, and contain generally less than about 2 parts, desirably less than about 1 part, and preferably less than about 0.5 part by weight or are entirely free thereof, based upon 100 total parts by weight of the one or more halogen-containing polymers or copolymers. The polymer compositions of the present invention are also generally substantially free of various Lewis acids such as boron trifluoride, aluminum chloride, zinc chloride, methyltin trichloride, dibutyltin dichloride, and the like. Such acids when contained in the polymeric composition are generally less than about 0.5 part, desirably less than about 0.1 part, and preferably less than about 0.01 part by weight per 100 total parts by weight of all halogen-containing polymers or copolymers.

Terpenes are generally unsaturated hydrocarbons having the formula $(C_5H_8)_x$ where x is 1 to about 10 and are acyclic or cyclic. Specific non-limiting examples of terpenes are disclosed in U.S. Pat. No. 3,242,133, incorporated by reference. The halogen-containing polymer compositions including an organic thiol are preferably free of a terpene and contain less than 1 part, and preferably less than about 0.5 part of terpene(s) per 100 parts by weight of the polymer.

The polymers utilized in the present invention include any organic chlorine- or bromine-containing polymers or resins in which the halogen is attached directly to a carbon atom. Polymers and/or monomers thereof useful to the present invention include, but are not limited to, poly(vinyl chloride) (PVC), poly(vinylidene chloride), poly(vinyl bromide), poly(vinylidene bromide), chlorinated poly(vinyl chloride), chlorinated polyethylene, chlorinated natural or synthetic rubber, polychloroprene, rubber hydrochloride, or chlorinated polystyrene, and combinations and copolymers thereof. The molecular weight of such polymers can vary over a wide range, and they generally have a number average molecular weight of from about 5,000 to about 1,000,000, or from about 10,000 to 100,000 for poly(vinyl chloride). Such polymers can also contain other plasticizers in addition to the compounds of the present invention, and where appropriate, such polymers can be plastisols, organisols, and the like.

The above noted chlorine- or bromine-containing polymers are made from monomers forming the same such as vinyl chloride, vinylidene chloride, and the like, or are a copolymer made from a mixture of monomers comprising, desirably, at least about 70% by weight of vinyl chloride, based on the total monomer weight. Examples of the copolymers include those made from vinyl chloride and from about 1 to about 30% of a copolymerizable ethylenically unsaturated monomer such as vinyl acetate, vinyl butyrate, vinyl benzoate, vinylidene chloride, diethyl fumarate, diethyl maleate, other alkyl fumarates and maleates, vinyl propionate, methyl acrylate, 2-ethylhexyl acrylate, butyl acrylate and other alkyl acrylates, methyl methacrylate, ethyl methacrylate, butyl methacrylate and other alkyl methacrylates, methyl alpha-chloroacrylate, styrene, trichloroethylene, vinyl ethers such as vinyl ethyl ether, vinyl chloroethyl ether and vinyl phenyl ether, vinyl ketones such as vinyl methyl ketone and vinyl phenyl ketone, 1-fluoro-2-chloroethylene, acrylonitrile, chloroacrylonitrile, allylidene diacetate, and chloroallylidene diacetate. Typical copolymers include vinyl chloride-vinyl acetate (e.g. 96:4 sold commercially as VYNW), vinyl chloride-vinyl acetate (e.g. 87:13), vinyl chloride-vinyl acetate-maleic anhydride (e.g. 86:13:1), vinyl chloride-vinylidene chloride (e.g. 95:5), vinyl chloride-diethyl fumarate (e.g. 95:5), and vinyl chloride-2-ethylhexyl acrylate (e.g. 80:20).

Preferred polymers include poly(vinyl chloride) and poly(vinyl bromide). Preferred copolymers include vinyl chloride-vinyl acetate, vinyl chloride-vinylidene chloride, and other vinyl chloride copolymers.

The organic thiol compounds according to the present invention are added to or blended with the above described polymers in any suitable amount, generally from about 1 to about 100 parts by weight per 100 total parts by weight of all of the one or more polymers or copolymers, depending on the desired properties of the final product such as being plasticized. As stated above, the organic thiol compounds of the present invention are particularly suitable for serving as both stabilizers and plasticizers. A semi-rigid composition of the present invention would desirably contain from about 1 to about 10, or about 15, or about 25 parts of the organic thiol compound per 100 parts by weight of a polymer defined above. A flexible composition of this invention contains from about 25, or about 30, or about 50, or about 60 to about 100 parts of the organic thiol compound per 100 parts of polymer utilized in the present invention. The organic thiol compounds can be incorporated into the resin by any one of many known methods that provide for uniform distribution of additives throughout resin compositions, such as, for example, mixing in an appropriate mill, mixer, or Banbury apparatus.

Depending on the end use, further additives in conventional or suitable amounts, known to the art and to the literature or to those of ordinary skill in the art, can be added to the above noted polymers, such as certain other stabilizers and costabilizers, lubricants, plasticizers, extenders, impact modifiers, fillers, pigments, antioxidants, dyes, ultraviolet light absorbing agents, densifying agents, and the like. For example, additional non-metal-containing heat stabilizers as known in the art are added to the polymer compositions in one embodiment. Examples include, but are not limited to, organic phosphites, nitrogen-containing stabilizers, epoxy compounds, and various polyols.

Advantageously, it has been found that the addition of epoxidized soybean oil (ESO) to compositions of the present invention usually increases the effectiveness of the organic thiols. Generally, epoxidized soybean oil is utilized in chlorine- or bromine-containing polymers as an HCl or HBr scavenger. Epoxidized soybean oil can be utilized in compositions of the present invention in an amount generally from about 1 to about 30 parts, desirably from about 2 to about 20 parts, and preferably from about 3 to about 10 parts by weight per 100 parts by weight of chlorine- or bromine-containing polymer. The advantageous effect obtained by utilizing both epoxidized soybean oil and the organic thiols of the present invention can be seen in some of the results listed in Table 4 hereinbelow, wherein it is shown that both the dynamic heat stability and decomposition time are improved when compared to those of compositions without the above stated compounds.

Various epoxy-based compounds are utilized in the present invention in place of the epoxidized soybean oil in generally the same amounts as noted herein. Examples of such epoxy compounds include, but are not limited to, epoxidized lard oil, epoxidized olive oil, epoxidized linseed oil, epoxidized castor oil, epoxidized peanut oil, epoxidized corn oil, epoxidized tung oil, epoxidized cottonseed oil, epichlorohydrin/Bisphenol A resins, phenoxy-propylene oxide, butoxypropylene oxide, epoxidized neopentylene oleate, glycidyl epoxystearate, epoxidized α-olefins, epoxidized glycidyl soyate, dicyclopentadiene dioxide, epoxidized butyl toluate, styrene oxide, dipentene dioxide, glycidol, vinyl cyclohexene dioxide, glycidyl ether of resorcinol, glycidyl ether of hydroquinone, glycidyl ether of 1,5-di-hydroxynaphthalene, epoxidized linseed oil fatty acids, allyl glycidyl ether, butyl glycidyl ether, cyclohexane oxide, 4-(2,3-epoxypropoxy) acetophenone, mesityl oxide epoxide, 2-ethyl-3-propyl glycidamide, glycidyl ethers of glycerine, pentaerythritol and sorbitol, and 3,4-epoxycyclohexane-1,1-dimethanol bis-9,10-epoxystearate.

As stated above, the organic thiols greatly enhance the heat stability of halogenated resins, which are known to undergo rapid thermal degradation under the conditions found in the processes to which these resins are subjected, such as, for example, calendering, extrusion, injection molding, and end usage at elevated temperatures. For example, poly(vinyl chloride) is known to undergo a rapid and sequential elimination of hydrogen chloride, or dehydrochlorination, at elevated process temperatures. Other halogenated resins are known to undergo similar dehydrohalogenation reactions. Dehydrochlorination in PVC can initiate at labile chlorines that are associated with irregularities in the molecular chain, such as branches or double bonds. Once free, the HCl promotes further degradation of the poly(vinyl chloride) through unzipping of additional hydrogen chloride from the polymer chain. The primary functions of heat stabilizers in PVC are to depress hydrogen chloride elimination and discoloration. In addition to functioning as heat stabilizers, the organic thiols of the present invention are often effective plasticizers and frequently serve or function as both a heat stabilizer and a plasticizer. Thus, in many polymer compositions such as PVC, organic thiols of the present invention serve as heavy-metal-free or metal-based-free stabilizers and plasticizers, a unique combination.

The organic thiols of the invention thus unexpectedly improve the processing properties of the polymers, further providing cost and efficiency improvements to resin processors. The disclosed thiols also generally do not cause odor problems associated with the processing of resins stabilized thereby and provide greatly increased resistance to resin yellowing associated with thermal degradation.

It is to be understood that both the aromatic and aliphatic organic thiols of the present invention can contain one or more substituents thereon, including but not limited to, alkoxy groups, ester groups such as carboethoxy or carbomethoxy, and halides such as chlorine, fluorine, bromine, and iodine. That is, various functional groups, such as those listed above, which do not react with the ester linkage or sulfhydryl groups can be utilized.

The following examples serve to illustrate, but not to limit, the present invention.

EXAMPLES

Example 1

An intimate mixture of PVC and di(2-ethylhexyl) 5-mercaptoisophthalate (0.044 mole per mole of PVC monomer units) was heated under argon at 170° C. for 1.5 hours. At the end of the heating period, the mixture retained its initial white color.

Example 2

An intimate mixture of PVC and pentaerythritol tetrakis (2-mercaptopropionate) (0.038 mole per mole of PVC monomer units) was heated under argon at 175–180° C. for 2.0 hours. At the end of the heating period, the mixture retained its initial white color.

Example 3

(Controls)

An intimate mixture of PVC and 1-dodecanethiol (0.044 mole per mole of PVC monomer units) was heated under argon at 170° C. for 1.5 hours. At the end of the heating period, the mixture was dark red-brown in color, a result that was indicative of extensive degradation. Essentially the same result was obtained when PVC was heated under the same conditions in the absence of a thiol or other additives.

Example 4

The following Table 3 is a comparative evaluation of the organic thiol bis(2-ethylhexyl) 5-mercaptoisophthalate in a typical poly(vinyl chloride) composition with current commercially utilized stabilizers. The formulations evaluated (A–F) were prepared by standard blending methods that are well-known to those skilled in the art. Properties of these formulations were determined by the standard ASTM methods that are identified under the heading "Test Description". The measurements reported show that the thiol plasticizer/stabilizer gave physical properties to the formulations which were comparable to those obtained with the common commercial plasticizer, DOP. Thus it is apparent that the thiol can function as the primary plasticizer for PVC without the need for additional plasticization. Moreover, the data in Table 3 show that the dynamic and static heat stability conferred by the thiol are equal to or better than those obtained with traditional amounts of commercial lead or barium-zinc heat stabilizers. Further, the tabulated data reveal that the stability obtained with the thiol can be achieved without the incorporation of an epoxidized soybean oil costabilizer. Finally, the data for formulations E and F indicate that the thermal stabilization effects of the thiol and the barium-zinc stabilizer are antagonistic, rather than additive or synergistic.

TABLE 3

Evaluation of Bis(2-ethylhexyl) 5-Mercaptoisophthalate in a Typical Poly(vinyl chloride) Composition

|  | A (control) | B (control) | C | D | E | F |
|---|---|---|---|---|---|---|
| Ingredient Description |  |  |  |  |  |  |
| OxyVinyls 455F (PVC) | 100.00 | 100.00 | 100.00 | 100.00 | 100.00 | 100.00 |
| DOP (Plasticizer) | 30.00 | 30.00 | — | — | — | 30.00 |
| Thiol Plasticizer/Stabilizer (Bis(2-ethylhexyl) 5-mercaptoisophthalate) | — | — | 35.00 | 30.00 | 30.00 | 5.00 |
| Epoxidized Soybean Oil (HCl scavenger) | 5.00 | 5.00 | — | 5.00 | 5.00 | — |
| General Purpose Ba/Zn Liquid (Stabilizer) | 3.00 | — | — | — | 3.00 | 3.00 |
| Dythal/Tribase Blend (Lead stabilizer) | — | 4.00 | — | — | — | — |
| Stearic Acid (Processing lubricant) | 0.10 | 0.10 | 0.10 | 0.10 | 0.10 | 0.10 |
| Total (Parts by weight) | 138.10 | 139.10 | 135.10 | 135.10 | 138.10 | 138.10 |
| Test Description |  |  |  |  |  |  |
| Hardness, Shore C (ASTM D 2240-86) | 85/74 | 86/75 | 94/85 | 94/86 | 95/91 | 86/75 |
| Specific Gravity (ASTM D 792-91) | 1.27 | 1.3 | 1.29 | 1.29 | 1.29 | 1.27 |
| Tensile Strength, PSI (ASTM D 638-91) | 3315 | 3472 | 3467 | 3421 | 3218 | 3322 |
| Elongation, % (ASTM D 638-91) | 338 | 305 | 281 | 328 | 306 | 341 |
| Dynamic Heat Stability, 205° C., 100 RPM, #5 Bowl, Minutes (ASTM D 2538-95) | 24 | 60 | 60 | 60 | 60 | 3 |
| Initial Yellow, 210° C., Minutes (ASTM D 2115-92) | 15 | 10 | 10 | 10 | 15 | 15 |
| Decomposition Time, 210° C., Minutes (ASTM D 2115-92) | 45 | >60 | >60 | >60 | 25 | 20 |

TABLE 4

Evaluation of Aliphatic Ester Thiols in a Typical Poly(vinyl chloride) Composition

|  | Control 1 | Control 2 | Trial 1 | Trial 2 | Trial 3 | Trial 4 |
|---|---|---|---|---|---|---|
| Ingredient Description |  |  |  |  |  |  |
| OxyVinyls 455F | 100.00 | 100.00 | 100.00 | 100.00 | 100.00 | 100.00 |
| DOP | 30.00 | 30.00 | — | — | — | — |
| Thiol-Adipate | — | — | 35.00 | 30.00 | — | — |
| Thiol-Succinate | — | — | — | — | 35.00 | 30.00 |
| Epoxidized Soybean Oil | 5.00 | — | — | 5.00 | — | 5.00 |
| General Purpose Ba/Zn Liquid | 3.00 | — | — | — | — | — |
| Dythal/Tribase Blend | — | 4.00 | — | — | — | — |
| Stearic Acid | 0.10 | 0.10 | 0.10 | 0.10 | 0.10 | 0.10 |
| Total (Parts by weight) | 138.10 | 134.10 | 135.10 | 135.10 | 135.10 | 135.10 |
| Test Description |  |  |  |  |  |  |
| Hardness, Shore C (ASTM D 2240-86) | 85/75 | 91/85 | 70/60 | 70/60 | 80/72 | 80/73 |
| Specific Gravity (ASTM D 792-91) | 1.27 | 1.32 | 1.3 | 1.3 | 1.27 | 1.27 |
| Tensile Strength, PSI (ASTM D 638-91) | 3482 | 3725 | 3759 | 3630 | 3588 | 3504 |
| Elongation, % (ASTM D 638-91) | 327 | 288 | 262 | 259 | 311 | 342 |
| Dynamic Heat Stability, 205° C., 100 RPM, #5 Bowl, Minutes (ASTM D 2538-95) | 19 | 29 | 57 | 58 | >60 | >60 |
| Initial Yellow, 210° C., Minutes (ASTM D 2115-92) | 15 | 10 | 15 | 15 | 15 | 15 |
| Decomposition Time, 210° C., Minutes (ASTM D 2115-92) | 45 | 60 | >60 | >60 | 50 | >60 |

Example 5

Aliphatic Ester Thiol Compounds

As can be seen in Table 4, aliphatic ester thiol compounds of the present invention were evaluated and directly compared to two control formulations containing a conventional plasticizer and two conventional stabilizers. The results show that both of the ester thiols are very good plasticizers, with the adipate thiol actually being more efficient as a plasticizer than DOP. Moreover, both of the ester thiols conferred dynamic and static heat stability to the formulations that were equal to or greater than those achieved with conventional amounts of commercial lead or barium-zinc stabilizers. When the succinate thiol was used, the static heat stability also was improved by the incorporation of 5 parts by weight of epoxidized soybean oil, which is well-known to be a scavenger for HCl. Furthermore, when used together with either the adipate thiol or the succinate thiol, the epoxidized soybean oil tended to prevent the formation of small bubbles in the test specimens during the static heat stability test. Neither of the aliphatic ester thiols caused strong or offensive odors during compounding or testing operations.

Example 6

Di-ester Ether Compounds Containing Sulfhydryl Groups

A static heat stability test was carried out with di(ethylene glycol) bis(3-mercaptobenzoate). 100 parts of poly(vinyl chloride) and 30 parts of the di(ethylene glycol) bis(3-mercaptobenzoate) (0.050 mole per mole of PVC monomer units) were intimately blended and heated under argon at 175–180° C. for two hours. At the end of the heating period, the mixture remained substantially as white as the starting blend, thus exhibiting no significant color change.

Example 7

Di-ester Ether Compounds Containing Sulfhydryl Groups

A static heat stability test was carried out with di(ethylene glycol) bis(2-mercaptobenzoate). 100 parts of poly(vinyl chloride) and 30 parts of the di(ethylene glycol) bis(2-mercaptobenzoate) (0.050 mole per mole of PVC monomer units) were intimately blended and heated under argon at 175–180° C. for two hours. At the end of the heating period, the mixture remained substantially as white as the starting blend.

Example 8

Comparison of Low Levels of Di(ethylene glycol) Bis(mercaptobenzoates) with Conventional Stabilizers Table 5 is a comparative evaluation of the organic thiols di(ethylene glycol) bis(2-mercaptobenzoate) and di(ethylene glycol) bis(3-mercaptobenzoate), utilized at low levels in a typical plasticized poly(vinyl chloride) composition, with current commercially utilized stabilizers. The formulations presented therein were prepared by standard blending methods which are well-known to those skilled in the art. Properties of these formulations were determined by the standard ASTM methods that are identified under the heading "Test Description." The data show that the dynamic heat stabilities conferred by the organic thiols are better than those obtained with traditional amounts of commercial lead or barium/zinc heat stabilizers. The excellent dynamic heat stability can be obtained with or without the incorporation of an epoxidized soybean oil costabilizer. However, the epoxidized soybean oil causes increases of the static decomposition times. As can be seen from Examples 6 and 7, the development time of initial yellow for PVC compositions can be increased by utilizing greater amounts of the organic thiol.

TABLE 5

Comparison of Low Levels of Di(ethylene glycol) Bis(mercaptobenzoates) with Conventional Stabilizers

| | Control 3 | Control 4 | Trial 5 | Trial 6 | Trial 7 | Trial 8 |
|---|---|---|---|---|---|---|
| Ingredient Description | | | | | | |
| OxyVinyls 455F | 100.00 | 100.00 | 100.00 | 100.00 | 100.00 | 100.00 |
| DOP | 30.00 | 30.00 | 30.00 | 30.00 | 30.00 | 30.00 |
| Di(ethylene glycol) bis(2-mercaptobenzoate) | — | — | 3.00 | 3.00 | — | — |
| Di(ethylene glycol) bis(3-mercaptobenzoate) | — | — | — | — | 3.00 | 3.00 |
| Epoxidized Soybean Oil | 5.00 | — | 5.00 | — | 5.00 | — |
| General Purpose Ba/Zn Liquid | 3.00 | — | — | — | — | — |
| Dythal/Tribase Blend | — | 4.00 | — | — | — | — |
| Stearic Acid | 0.10 | 0.10 | 0.10 | 0.10 | 0.10 | 0.10 |
| Total (Parts by weight) | 138.10 | 134.10 | 138.10 | 133.10 | 138.10 | 133.10 |
| Test Description | | | | | | |
| Dynamic Heat Stability, 205° C., 100 RPM, #5 Bowl, Minutes (ASTM D 2538-95) | 14 | 22 | >60 | >60 | >60 | >60 |
| Initial Yellow, 210° C., Minutes (ASTM D 2115-92) | 20 | 10 | 5 | 5 | 10 | 10 |
| Decomposition Time, 210° C., Minutes (ASTM D 2115-92) | 35 | >60 | 40 | 20 | 45 | 20 |

Example 9

Comparison of Low Levels of Pentaerythritol 2-Ethylhexanoate Tris(2-mercaptopropionate) and Dipentaerythritol Hexakis(3-mercaptopropionate) with Conventional Stabilizers Table 6 is a comparative evaluation of the organic thiols pentaerythritol 2-ethylhexanoate tris(2-mercaptopropionate) and dipentaerythritol hexakis(3-mercaptopropionate), utilized at low levels in a typical plasticized poly(vinyl chloride) composition, with current commercially utilized stabilizers. The formulations presented therein were prepared by standard blending methods which are well-known to those skilled in the art. Properties of these formulations were determined by the standard ASTM methods that are identified under the heading "Test Description." The data show that the dynamic heat stabilities conferred by the organic thiols are better than those obtained with traditional amounts of commercial lead or barium/zinc heat stabilizers. The excellent dynamic heat stability can be obtained with or without the incorporation of an epoxidized soybean oil costabilizer. However, the epoxidized soybean oil causes increases of the times to initial yellowing, and in the case of dipentaerythritol hexakis(3-mercaptopropionate), epoxidized soybean oil increases both the dynamic heat stability and the static decomposition time.

TABLE 6

Comparison of Low Levels of Pentaerythritol 2-Ethylhexanoate Tris(2-mercaptopropionate) and Dipentaerythritol Hexakis(3-mercaptopropionate) with Conventional Stabilizers

| | Control 1 | Control 2 | Trial 1 | Trial 2 | Trial 3 | Trial 4 |
|---|---|---|---|---|---|---|
| Ingredient Description | | | | | | |
| OxyVinyls 455F | 100.00 | 100.00 | 100.00 | 100.00 | 100.00 | 100.00 |
| DOP | 30.00 | 30.00 | 30.00 | 30.00 | 30.00 | 30.00 |
| Pentaerythritol 2-ethylhexanoate tris(2-mercaptopropionate) | — | — | 3.00 | 3.00 | — | — |
| Dipentaerythritol hexakis(3-mercaptopropionate) | — | — | — | — | 3.00 | 3.00 |
| Epoxidized Soybean Oil | 5.00 | — | 5.00 | — | 5.00 | — |
| General Purpose Ba/Zn Liquid | 3.00 | — | — | — | — | — |
| Dythal/Tribase Blend | — | 4.00 | — | — | — | — |
| Stearic Acid | 0.10 | 0.10 | 0.10 | 0.10 | 0.10 | 0.10 |
| Total (Parts by weight) | 138.10 | 134.10 | 138.10 | 133.10 | 138.10 | 133.10 |
| Test Description | | | | | | |
| Dynamic Heat Stability, 205° C., 100 RPM, #5 Bowl, Minutes (ASTM D 2538-95) | 21 | 23 | >60 | >60 | >60 | 41 |
| Initial Yellow, 210° C., Minutes (ASTM D 2115-92) | 20 | 15 | 10 | 5 | 15 | 10 |
| Decomposition Time, 210° C., Minutes (ASTM D 2115-92) | 45 | >60 | 30 | 30 | >60 | 40 |

Example 10

Color Stabilization by Low Levels of Mercaptophenylcarboxylate Heat Stabilizers Table 7 is a comparative evaluation of mercaptophenylcarboxylate organic thiols disclosed as in the present invention. A blend of the ingredients listed for each trial was heated under argon at 175° C. to about 180° C. for 2.0 h. The color stability results are listed in the table. Under the same conditions, PVC containing no additives acquired a very dark red-brown color.

mercaptophenylacetate) (major isomer), pentaerythritol tetrakis(3-mercaptophenylacetate) (major isomer), and di(ethylene glycol) bis(mercaptophenylacetate), utilized at low levels in a typical plasticized poly(vinyl chloride) composition, with current commercially utilized stabilizers. The formulations presented therein were prepared by standard blending methods which are well-known to those skilled in the art. Properties of these formulations were determined by the standard ASTM methods that are identified under the heading "Test Description." The data show

TABLE 7

Color Stabilization by Low Levels of Mercaptophenylcarboxylate Heat Stabilizers

| | Trial 1 | Trial 2 | Trial 3 | Trial 4 | Trial 5 | Trial 6 | Trial 7 | Trial 8 | Trial 9 | Trial 10 |
|---|---|---|---|---|---|---|---|---|---|---|
| Ingredient Description | | | | | | | | | | |
| PVC | 100.00 | 100.00 | 100.00 | 100.00 | 100.00 | 100.00 | 100.00 | 100.00 | 100.00 | 100.00 |
| Pentaerythritol tetrakis(4-mercaptophenylacetate) (major isomer)[a] | 3.00 | 3.00 | — | — | — | — | — | — | — | — |
| Pentaerythritol tetrakis (3-mercaptophenylacetate) (major isomer)[b] | — | — | 3.00 | 3.00 | — | — | — | — | — | — |
| Di(ethylene glycol) bis(mercaptophenylacetate) | — | — | — | — | 3.00 | 3.00 | — | — | — | — |
| Tri(ethylene glycol) bis(mercaptophenylacetate) | — | — | — | — | — | — | 3.00 | 3.00 | — | — |
| 1,3-Propanediol bis(mercaptophenylacetate) | — | — | — | — | — | — | — | — | 3.00 | 3.00 |
| Epoxidized Soybean Oil | 5.00 | — | 5.00 | — | 5.00 | — | 5.00 | — | 5.00 | — |
| Total (Parts by weight) | 108.00 | 103.00 | 108.00 | 103.00 | 108.00 | 103.00 | 108.00 | 103.00 | 108.00 | 103.00 |
| Test Description | | | | | | | | | | |
| Visual Color | Pale yellow-brown | Pale yellow-brown | Pale yellow | Pale yellow | Off-white | Off-white | Very pale yellow | Very pale yellow | Very pale yellow | Very pale yellow |

[a]Mixture also contained the 3-isomer
[b]Mixture also contained the 4-isomer

Example 11

Comparison of Low Levels of Mercaptophenylcarboxylates with Conventional Stabilizers Table 8 is a comparative evaluation of the mercaptophenylcarboxylate organic thiols pentaerythritol tetrakis(4- that the dynamic heat stabilities conferred by the organic thiols are better than those obtained with traditional amounts of commercial lead or barium/zinc heat stabilizers. The excellent dynamic heat stability can be obtained with or without the incorporation of an HCl scavenger such as epoxidized soybean oil.

TABLE 8

Comparison of Low Levels of Mercaptophenylcarboxylate Organic Thiols with Conventional Stabilizers

| | Control 1 | Control 2 | Trial 1 | Trial 2 | Trial 3 | Trial 4 | Trial 5 | Trial 6 |
|---|---|---|---|---|---|---|---|---|
| Ingredient Description | | | | | | | | |
| PVC (OxyVinyls 455F) | 100.00 | 100.00 | 100.00 | 100.00 | 100.00 | 100.00 | 100.00 | 100.00 |
| DOP | 30.00 | 30.00 | 30.00 | 30.00 | 30.00 | 30.00 | 30.00 | 30.00 |
| Pentaerythritol tetrakis(4-mercaptophenylacetate) (major isomer)[a] | — | — | 3.00 | 3.00 | — | — | — | — |

TABLE 8-continued

Comparison of Low Levels of Mercaptophenylcarboxylate Organic Thiols with Conventional Stabilizers

|  | Control 1 | Control 2 | Trial 1 | Trial 2 | Trial 3 | Trial 4 | Trial 5 | Trial 6 |
|---|---|---|---|---|---|---|---|---|
| Pentaerythritol tetrakis (3-mercaptophenylacetate) (major isomer)[b] | — | — | — | — | 3.00 | 3.00 | — | — |
| Di(ethylene glycol) bis(mercaptophenylacetate) | — | — | — | — | — | — | 3.00 | 3.00 |
| General Purpose Ba/Zn Liquid | 3.00 | — | — | — | — | — | — | — |
| Dythal/Tribase Blend | — | 4.00 | — | — | — | — | — | — |
| Epoxidized Soybean Oil | — | — | 5.00 | — | 5.00 | — | 5.00 | — |
| Stearic acid | 0.10 | 0.10 | 0.10 | 0.10 | 0.10 | 0.10 | 0.10 | 0.10 |
| Total (Parts by weight) | 133.10 | 134.10 | 138.10 | 133.10 | 138.10 | 133.10 | 138.10 | 133.10 |
| Test Description |  |  |  |  |  |  |  |  |
| Dynamic Heat Stability, 205° C., 100 RPM, #5 Bowl, Minutes (ASTM D 2538-95) | 17 | 25 | >60 | >60 | >60 | >60 | >60 | >60 |
| Initial Yellow, 210° C., Minutes (ASTM D 2115-92) | 20 | 15 | 10 | 10 | 10 | 10 | 10 | 10 |
| Decomposition Time, 210° C., Minutes (ASTM D 2115-92) | 35 | >60 | 40 | 30 | 40 | 25 | 45 | 25 |

[a]Mixture also contained the 3-isomer
[b]Mixture also contained the 4-isomer

In accordance with the patent statutes, the best mode and preferred embodiments have been set forth, and the scope of the present invention is not limited thereto, but rather by the scope of the attached claims.

What is claimed is:

1. A polymer composition comprising:
   a chlorine-containing or bromine-containing polymer; and
   a heat stabilizer component consisting of a) an organic thiol compound having the formula:

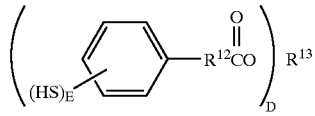

wherein E is 1 to about 5, wherein $R^{12}$ is a straight chain or branched alkylene having from 1 to about 15 carbon atoms, wherein $R^{13}$ is i) a linear, cyclo-, or branched alkyl or alkylene group, having from 1 to about 25 carbon atoms, or ii) an aralkyl or aralkylene group having from 7 to about 25 carbon atoms, or said i) or ii) having at least one heteroatom, and wherein D is 1 to about 10; and optionally b) a non-metal-containing heat stabilizer free of a terpene compound,
   wherein said organic thiol compound is present in an amount from about 1 to about 100 parts by weight per 100 parts by weight of said polymer.

2. A polymer composition according to claim 1, wherein D is 2 to about 6.

3. A polymer composition according to claim 2, wherein said organic thiol is di(ethylene glycol) bis(3-mercaptophenylacetate), di(ethylene glycol) bis(4-mercaptophenylacetate), tri(ethylene glycol) bis(3-mercaptopheflylacetate), tri(ethylene glycol) bis(4-mercaptophenylacetate), 1,3-propanediol bis(3-mercaptophenylacetate), 1,3-propanediol bis(4-mercaptophenylacetate), pentaeryth ritol tetrakis(3-mercaptophenylacetate), pentaerythritol tetrakis(4-mercaptophenylacetate), 4,4'-dimethyloldiphenylether bis(mercaptophenylacetate), o-, m-, or p-xylene-α,α'-diol bis(mercaptophenylacetate) or a combination thereof.

4. A polymer composition according to claim 2, wherein E is 1 to 4, and wherein said heteroatom comprises an ethereal oxygen atom.

5. A polymer composition according to claim 1, wherein said polymer is poly(vinyl chloride), poly(vinylidene chloride), poly(vinyl bromide), poly(vinylidene bromide), chlorinated poly(vinyl chloride), chlorinated polyethylene, chlorinated natural or synthetic rubber, polychloroprene, rubber hydrochloride, chlorinated polystyrene, or copolymers thereof, or combinations thereof.

6. A polymer composition according to claim 5, wherein the amount of said organic thiol is from about 1 to about 50 parts, or about 50 parts to about 100 parts per 100 parts by weight of said polymer.

7. A polymer composition according to claim 5, wherein said composition further includes said non-metal-containing heat stabilizer free of a terpene compound.

8. A polymer composition according to claim 7, wherein said non-metal-containing heat stabilizer is epoxidized soybean oil, and wherein said epoxidized soybean oil is present in an amount from about 1 to about 30 parts by weight per 100 parts by weight of said polymer.

9. A polymer composition comprising:
   a chlorine containing or bromine containing polymer; and
   an organic thiol compound having the formula:

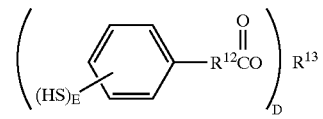

wherein E is 1 to about 5, wherein $R^{12}$ is a straight chain or branched alkylene having from 1 to about 15 carbon atoms, wherein $R^{13}$ is i) a linear, cyclo-, or branched alkyl or alkylene group, having from 1 to about 25 carbon atoms, or ii) an aralkyl or aralkylene group having from 7 to about 25 carbon atoms, or said i) or ii) having at least one heteroatom, and wherein D is 1 to about 10; wherein said polymer composition is free of a Lewis acid, wherein said polymer composition is free of a metal-containing heat stabilizer, and wherein said polymer composition is also free of a terpene compound.

10. A polymer composition according to claim 9, wherein D is 2 to about 6.

11. A polymer composition according to claim 10, wherein said organic thiol is di(ethylene glycol) bis(3-mercaptophenylacetate), di(ethylene glycol) bis(4-mercaptophenylacetate), tri(ethylene glycol) bis(3-mercaptophenylacetate), tri(ethylene glycol) bis(4-mercaptophenylacetate), 1,3-propanediol bis(3-mercaptophenylacetate), 1,3-propanediol bis(4-mercaptophenylacetate), pentaerythritol tetrakis(3-mercaptophenylacetate), pentaerythritol tetrakis(4-mercaptophenylacetate), 4,4'-dimethyloldiphenylether bis(mercaptophenylacetate), o-, m-, or p-xylene-α,α'-diol bis(mercaptophenylacetate) or a combination thereof.

12. A polymer composition according to claim 11, wherein E is 1 to 4, and wherein said heteroatom comprises an ethereal oxygen atom.

13. A polymer composition according to claim 12, wherein said polymer is poly(vinyl chloride), poly(vinylidene chloride), poly(vinyl bromide), poly(vinylidene bromide), chlorinated poly(vinyl chloride), chlorinated polyethylene, chlorinated natural or synthetic rubber, polychloroprene, rubber hydrochloride, chlorinated polystyrene, or copolymers thereof, or combinations thereof.

14. A polymer composition according to claim 13, wherein the amount of said organic thiol is from about 1 to about 50 parts, or about 50 parts to about 100 parts by weight per 100 parts by weight of said polymer.

15. A polymer composition according to claim 14, wherein said composition further includes a non-metal-containing heat stabilizer which is free of a terpene compound.

16. A polymer composition according to claim 15, wherein said non-metal-containing heat stabilizer is epoxidized soybean oil, and wherein said epoxidized soybean oil is present in an amount from about 1 to about 30 parts by weight per 100 parts by weight of said polymer.

17. An organic thiol, having the formula

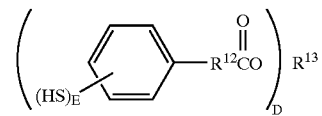

wherein E is 1 to about 5, wherein $R^{12}$ is a straight chain or branched alkylene having from 1 to about 15 carbon atoms, wherein $R^{13}$ is i) a linear, cyclo-, or branched alkyl or alkylene group, having from 1 to about 25 carbon atoms, or ii) an aralkyl or aralkylene group having from 7 to about 25 carbon atoms, or said i) or ii) having at least one heteroatom, and wherein D is 2 to about 10.

18. An organic thiol according to claim 17, wherein D is 2 to 4, and wherein E is 1 to about 4.

19. An organic thiol according to claim 18, wherein said organic thiol is di(ethylene glycol) bis(3-mercaptophenylacetate), di(ethylene glycol) bis(4-mercaptophenylacetate), tri(ethylene glycol) bis(3-mercaptophenylacetate), tri(ethylene glycol) bis(4-mercaptophenylacetate), 1,3-propanediol bis(3-mercaptophenylacetate), 1,3-propanediol bis(4-mercaptophenylacetate), pentaerythritol tetrakis(3-mercapto-phenylacetate), pentaerythritol tetrakis(4-mercaptophenylacetate), 4,4'-dimethyloldi-phenylether bis(mercaptophenylacetate), o-, m-, or p-xylene-α,α'-diol bis(mercapto-phenylacetate) or a combination thereof.

20. An organic thiot according to claim 19, wherein said heteroatom comprises an oxygen atom, and wherein $R^{12}$ is 1 to about 6 carbon atoms.

* * * * *

UNITED STATES PATENT AND TRADEMARK OFFICE
CERTIFICATE OF CORRECTION

PATENT NO.      : 6,927,247 B2
DATED           : August 9, 2005
INVENTOR(S)     : William Herbert Starnes et al.

It is certified that error appears in the above-identified patent and that said Letters Patent is hereby corrected as shown below:

Title page,
Item [56], References Cited, OTHER PUBLICATIONS,
"Nonmetallic Primary Heat Stabilizers..." reference, please replace "Scicne" with -- Science --.

Column 6,
Line 49, after "preferably" insert -- at --.

Column 13,
Line 22, please replace "(t, 4H, C$\underline{H}$$_2$C$\underline{H}$$_2$CO$_2$ R)" with -- (t, 4H, C$\underline{H}$$_2$CH$_2$CO$_2$ R) --.
Line 23, please replace "OCH$_2$(CH$_2$)$_4$)" with -- OCH$_2$(C$\underline{H}$$_2$)$_4$) --.
Line 24, please replace "(quartet, 4H, C$\underline{H}$$_2$S$\underline{H}$)" with -- (quartet, 4H, C$\underline{H}$$_2$SH) --.
Line 27, please replace "(C$\underline{O}$$_2$ R)" with -- ($\underline{C}$O$_2$ R) --.

Column 14,
Line 4, please replace "(C$\underline{H}$$_2$CO$_2$R)" with -- ($\underline{C}$H$_2$CO$_2$R) --.
Line 38, please replace "(d of d, 4H, SH)" with -- (d of d, 4H, S$\underline{H}$) --.
Line 39, please replace "(C$\underline{H}$$_2$O)" with -- ($\underline{C}$H$_2$O) --.

Column 15,
Line 11, please replace "C$\underline{H}$$_2$O" with -- C$\underline{H}$$_2$O --.
Lines 13 and 14, please replace "(t, 6H, CH$_3$C$\underline{H}$$_2$)" with -- (t, 6H, C$\underline{H}$$_3$CH$_2$) --.

Column 17,
Line 22, please replace "(C$\underline{H}$$_2$ OCH$_2$)" with -- ($\underline{C}$H$_2$O$\underline{C}$H$_2$) --.

Column 22,
Lines 28, and 47, please replace "(4-isomer CH$_2$C==O)" with -- (4-isomer $\underline{C}$H$_2$C==O) --.
Lines 29 48 and 62, please replace "(3-isomer CH$_2$C==O)" with -- (3-isomer $\underline{C}$H$_2$C==O) --.
Lines 29 and 48, please replace "[C(CH$_2$)$_4$]" with -- [$\underline{C}$(CH$_2$)$_4$] --.
Line 63, please replace "(CH$_2$OC==O)" with -- ($\underline{C}$H$_2$OC==O) --.
Line 63, please replace "(CH$_2$CH$_2$O$_2$C)" with -- ($\underline{C}$H$_2$CH$_2$O$_2$C) --.
Line 64, please replace "(CH$_2$OCH$_2$CH$_2$O$_2$C)" with -- ($\underline{C}$H$_2$OCH$_2$CH$_2$O$_2$C) --.

Column 23,
Lines 19 and 62, please replace "(4-isomer CH$_2$C==O)" with -- (4-isomer $\underline{C}$H$_2$C==O) --.
Line 19, please replace "(3-isomer CH$_2$C==O)" with -- (3-isomer $\underline{C}$H$_2$C==O) --.
Line 20, please replace "(CH$_2$OC==O)" with -- ($\underline{C}$H$_2$OC==O) --.

UNITED STATES PATENT AND TRADEMARK OFFICE
CERTIFICATE OF CORRECTION

PATENT NO. : 6,927,247 B2
DATED : August 9, 2005
INVENTOR(S) : William Herbert Starnes et al.

It is certified that error appears in the above-identified patent and that said Letters Patent is hereby corrected as shown below:

Column 24,
Line 29, please replace "(m, 2H, $CH_2CH_2CH_2$)" with -- (m, 2H, $CH_2C\underline{H}_2CH_2$) --.
Line 33, please replace "($CH_2CH_2CH_2$)" with -- ($CH_2\underline{C}H_2CH_2$) --.
Line 34, please replace "(4-isomer $CH_2C==O$)" with -- (4-isomer $\underline{C}H_2C==O$) --.
Line 34, please replace "(3-isomer $CH_2C==O$)" with -- (3-isomer $\underline{C}H_2C==O$) --.

Column 35,
Line 60, please replace "mercaptopheflylacetate" with -- mercaptophenylacetate --.
Line 63, please replace "pentaeryth ritol" with -- pentaerythritol --.

Column 36,
Line 33, please replace "polychioroprene" with -- polychloroprene --.

Column 38,
Line 27, please replace "1,3-propaned iol" with -- 1,3-propanediol --.
Lines 29 and 32, please replace "mercapto-phenylacetate" with
-- mercaptophenylacetate --.
Line 30, please replace "4,4'-dimethyloldi-phenylether" with
-- 4,4'-dimethyloldiphenylether --.
Line 33, please replace "thiot" with -- thiol --.

Signed and Sealed this

Twenty-ninth Day of November, 2005

JON W. DUDAS
*Director of the United States Patent and Trademark Office*